(12) United States Patent
Espinheira De Sá Maciel et al.

(10) Patent No.: US 11,033,526 B2
(45) Date of Patent: Jun. 15, 2021

(54) CITALOPRAM OR ESCITALOPRAM FOR USE IN THE TREATMENT OF NEURODEGENERATIVE DISEASES

(71) Applicant: UNIVERSIDADE DO MINHO, Braga (PT)

(72) Inventors: Patricia Espinheira De Sá Maciel, Oporto (PT); Andreia Cristiana Teixeira De Castro, Braga (PT); Ana Luísa De Jales Monteiro De Sousa, Arcozelo (PT); Ana Sofia Teixeira Esteves, Villa Nova de Gaia (PT); Nuno Jorge Carvalho Sousa, Oporto (PT)

(73) Assignee: UNIVERSIDADE DO MINHO, Braga (PT)

( * ) Notice: Subject to any disclaimer, the term of this patent is extended or adjusted under 35 U.S.C. 154(b) by 5 days.

(21) Appl. No.: 15/559,241

(22) PCT Filed: Mar. 17, 2016

(86) PCT No.: PCT/IB2016/051511
§ 371 (c)(1),
(2) Date: Sep. 18, 2017

(87) PCT Pub. No.: WO2016/147146
PCT Pub. Date: Sep. 22, 2016

(65) Prior Publication Data
US 2019/0029992 A1 Jan. 31, 2019

(30) Foreign Application Priority Data

Mar. 17, 2015 (PT) .......................................... 108294
Jun. 24, 2015 (EP) ..................................... 15173723

(51) Int. Cl.
*A61K 31/343* (2006.01)
*A61P 25/28* (2006.01)
*A61K 9/00* (2006.01)

(52) U.S. Cl.
CPC .......... *A61K 31/343* (2013.01); *A61K 9/0053* (2013.01); *A61P 25/28* (2018.01)

(58) Field of Classification Search
CPC ...... A61K 31/343; A61K 9/0053; A61P 25/28
USPC ...................................................... 514/469
See application file for complete search history.

(56) References Cited

FOREIGN PATENT DOCUMENTS

| WO | 2007124757 A2 | 11/2007 |
| WO | WO20120374567 | * 3/2012 |
| WO | 2014093114 A1 | 6/2014 |

OTHER PUBLICATIONS

Menza et al. J Neuropsychiatry Clin (2004), vol. 16, pp. 315-319 (Year: 2004).*
Figiel et al. Mol Neurobiolo (2012) vol. 46, pp. 393-429 (Year: 2012).*
Matos et al. Progress in Neurobiology (2011), vol. 95 pp. 26-48. (Year: 2011).*
Beglinger et al. "Results of the citalopram to enhance cognition in Huntington disease trial." Movement Disorders 29.3 (2014): 401-405.
D'Abreu et al. "Caring for Machado—Joseph disease: current understanding and how to help patients." Parkinsonism & related disorders 16.1 (2010): 2-7. doi:10.1016/j.parkreldis.2009.08.012. 12 pages.
Do Carmo Costa et al. "Toward understanding Machado—Joseph disease." Progress in Neurobiology 97.2 (2012): 239-257. doi:10.1016/j.pneurobio.2011.11.006. 44 pages.
International Search Report and Written Opinion for International Patent Application No. PCT/IB2016/051511 dated Jun. 6, 2016. 11 pages.
Mandrioli et al. "Selective serotonin reuptake inhibitors (SSRIs): therapeutic drug monitoring and pharmacological interactions." Current Medicinal Chemistry 19.12 (2012): 1846-1863.
Monte et al. "Use of fluoxetine for treatment of Machado-Joseph disease: an open-label study." Acta Neurologica Scandinavica 107.3 (2003): 207-210.
Silva-Fernandes et al. "Chronic treatment with 17-DMAG improves balance and coordination in a new mouse model of Machado-Joseph disease." Neurotherapeutics 11.2 (2014): 433-449.
Takei et al. "Beneficial effects of tandospirone on ataxia of a patient with Machado-Joseph disease." Psychiatry and clinical neurosciences 56.2 (2002): 181-185.
Teixeira-Castro et al. "Neuron-specific proteotoxicity of mutant ataxin-3 in C. elegans: rescue by the DAF-16 and HSF-1 pathways." Human molecular genetics 20.15 (2011): 2996-3009.
Teixeira-Castro et al. "Serotonergic signalling suppresses ataxin 3 aggregation and neurotoxicity in animal models of Machado-Joseph disease." Brain 138.11 (2015): 3221-3237. 17 pages.

* cited by examiner

*Primary Examiner* — Taina D Matos Negron
(74) *Attorney, Agent, or Firm* — Leasons Ellis LLP

(57) ABSTRACT

Citalopram or escitalopram, pharmaceutically acceptable salts or derivatives thereof for use in the treatment of neurodegenerative diseases The disclosure subject matter is related to the use of citalopram or escitalopram, pharmaceutically acceptable salts or derivatives thereof, in the treatment of neurodegenerative diseases that are positively influenced by the decrease of protein misfolding and/or aggregation, in particular by oral administration.

8 Claims, 25 Drawing Sheets

| Strain (n)* | Median lifespan (days) | s.e.m. (days) | Mean lifespan (days) | s.e.m. (days) | Control strain (n)* | Median lifespan (days) | s.e.m. (days) | Mean lifespan (days) | s.e.m. (days) | p value (Log Rank, Mantel-Cox) |
|---|---|---|---|---|---|---|---|---|---|---|
| daf-16 (70) | 15 | 0.42 | 15.09 | 0.384 | WT_N2 (77) | 19 | 0.50 | 18.97 | 0.499 | <0.0001 |
| daf-2 (73) | 37 | 1.14 | 35.81 | 0.894 | WT_N2 (77) | 19 | 0.50 | 18.97 | 0.499 | <0.0001 |
| AT3q130 (91) | 17 | 0.36 | 17.08 | 0.448 | WT_N2 (77) | 19 | 0.50 | 18.97 | 0.499 | 0.008 |
| N2::cit (90) | 18 | 0.52 | 18.08 | 0.382 | WT_N2 (77) | 19 | 0.50 | 18.97 | 0.499 | 0.073 |
| AT3q130::cit (86) | 19 | 0.45 | 19.34 | 0.509 | AT3q130 (91) | 17 | 0.36 | 17.08 | 0.448 | 0.002 |
| AT3q130::cit (86) | 19 | 0.45 | 19.34 | 0.509 | WT_N2 (77) | 19 | 0.50 | 18.97 | 0.499 | 0.639 | n- number of animals

Fig. 2E

CITALOPRAM OR ESCITALOPRAM FOR USE IN THE TREATMENT OF NEURODEGENERATIVE DISEASES

CROSS-REFERENCE TO RELATED APPLICATIONS

This application is a U.S. National Stage Application under 35 U.S.C. § 371 of International Patent Application No. PCT/IB2016/051511, filed Mar. 17, 2016, which claims priority to European Application No. 15173723.6, filed Jun. 24, 2015, and Portuguese Application No. 108294, filed Mar. 17, 2015, which are hereby incorporated by reference in their respective entireties.

TECHNICAL FIELD

The present disclosure relates to the treatment of neurodegenerative diseases using citalopram or escitalopram as active ingredient, in particular polyglutamine diseases, in particular Machado-Joseph disease (MJD) or Spinocerebellar ataxia type 3 (SCA3).

TECHNICAL BACKGROUND

Polyglutamine diseases are a class of dominantly inherited neurodegenerative disorders for which there is no effective treatment. The expansion of trinucleotide CAG repeats causes hereditary adult-onset neurodegenerative disorders such as Huntington's disease (HD), spinobulbar muscular atrophy, dentatorubral-pallidoluysian atrophy and six forms of spinocerebellar ataxia. MJD/SCA3, the most common dominantly inherited SCA worldwide, is characterized by ataxia, ophthalmoplegia and pyramidal signs, associated with dystonia, spasticity, peripheral neuropathy and amyotrophy, without cognitive decline. Pathologically, there is degeneration of the deep nuclei of the cerebellum, pontine and subthalamic nuclei, substantia nigra and spinocerebellar nuclei. The genetic basis of MJD is the expansion of a polyglutamine (polyQ) tract within the protein ataxin-3 (ATXN3). When the polyQ tract exceeds 60 consecutive glutamines ATXN3 becomes highly aggregation-prone, leading to an imbalance in cellular proteostasis, as aggregation-associated proteotoxicity dominates over folding and clearance.

Currently there is no treatment for MJD that effectively slows disease progression. Efforts to improve patient quality of life and to sustain independence address the restless legs and extrapyramidal syndromes, treatment of cramps and of the effects of fatigue (D'Abreu, A., Franca, M. C., Jr., Paulson, H. L. & Lopes-Cendes, I. Caring for Machado-Joseph disease: current understanding and how to help patients. Parkinsonism Relat Disord 16, 2-7 (2010)). Not yet translated to clinical practice are therapeutic strategies that include pharmacologic chaperones and kinetic stabilizer approaches, and the use of small molecules or gene targeting to manipulate the concentration, conformation, and/or location of ATXN3 (Costa M. do, C. & Paulson, H. L. Toward understanding Machado-Joseph disease. Prog Neurobiol 97, 239-257 (2012)). For many proposed therapies, translation into clinical practice will be further limited by human safety and lack of toxicity upon chronic treatment. The traditional approach to drug discovery, which involves de novo identification and validation of new molecular targets is costly and time-consuming, thus limiting the number of new drugs introduced into the clinic. Moreover, as the average time required for drug development continues to increase, there has been renewed interest in drug repurposing strategies. On the other hand, over the past years, the primary cause of new drug candidate failures has been low therapeutic efficacy in clinical trials. Among the most frequently proposed reasons for this shortcoming is the lack of translation of in vitro and recombinant drug activity to therapeutic effect, in vivo, in whole organism systems.

These facts are disclosed in order to illustrate the technical problem addressed by the present disclosure.

GENERAL DESCRIPTION

Here evidence is provided to the fact that activation of serotonergic signalling is beneficial in animal models of MJD. Citalopram, a selective serotonin re-uptake inhibitor (SSRI), was identified as having beneficial effects, reducing neuronal dysfunction and protein aggregation in a previously described *Caenorhabditis elegans* (*C. elegans*) model of mutant ataxin-3 induced neurotoxicity (Teixeira-Castro, A. et al. Neuron-specific proteotoxicity of mutant ataxin-3 in *C. elegans*: rescue by the DAF-16 and HSF-1 pathways. Hum Mol Genet 20, 2996-3009 (2011)). MOD-5, the *C. elegans* ortholog of the serotonin transporter and cellular target of citalopram, and the serotonin receptors SER-1 and SER-4 were shown to be strong genetic modifiers of MJD and necessary for therapeutic efficacy. Moreover, chronic treatment of CMVMJD135 mice (Silva-Fernandes, A. et al. Chronic Treatment with 17-DMAG Improves Balance and Coordination in A New Mouse Model of Machado-Joseph Disease. Neurotherapeutics (2014)) with citalopram reduced ATXN3 neuronal inclusions and astrogliosis, strikingly ameliorated motor symptoms, and rescued diminished body weight. These results reveal that small molecule modulation of serotonergic signalling represents a therapeutic target for MJD. Moreover, the finding that serotonin recapture inhibition modulates proteotoxicity can be relevant for other protein conformation disorders.

The disclosure subject matter is related to the use of citalopram or escitalopram, pharmaceutically acceptable salts or derivatives thereof, in the treatment of neurodegenerative diseases that are positively influenced by the decrease of protein misfolding and/or aggregation, namely, for improving motor symptoms, namely lack of: balance, motor coordination, and/or motor performance of patients.

In an embodiment, the use of citalopram or escitalopram is for the use in the prevention and delay of neurodegenerative diseases.

In an embodiment, citalopram or escitalopram is for the use in the treatment of neurodegenerative diseases wherein said diseases are positively influenced by the control of protein misfolding and/or aggregation.

In an embodiment, citalopram or escitalopram is for the use in the treatment of neurodegenerative diseases wherein said diseases are positively influenced by the control of protein misfolding and/or aggregation, wherein said control is the control of protein aggregation caused by an expansion in the polyglutamine segment of the affected proteins.

In an embodiment, citalopram or escitalopram is for the use in the treatment of spinocerebellar ataxia type 3, also known as Machado-Joseph disease.

In an embodiment, citalopram or escitalopram is for the use in the treatment of Huntington's disease, Parkinson disease, amyotrophic lateral sclerosis disease, Machado-Joseph disease, spinobulbar muscular atrophy, dentatorubralpallidoluysian atrophy, and spinocerebellar ataxia type 1, spinocerebellar ataxia type 2, spinocerebellar ataxia type 6, spinocerebellar ataxia type 7 and spinocerebellar ataxia type 17. Namely, for improving motor symptoms, namely lack of: balance, motor coordination, and/or motor performance of patients.

The disclosed subject matter also relates to a pharmaceutical composition comprising citalopram, escitalopram or their salts in a therapeutically effective amount and a pharmaceutical acceptable carrier, adjuvant, excipient or mixtures thereof for use in the treatment of neurodegenerative diseases.

In an embodiment, the composition comprises the administration of a daily dosage to a person with a neurodegenerative disease that is positively influenced by the decrease of protein misfolding and/or aggregation, wherein the dosage amount is less than 40 mg/day, preferably from 20-40 mg/day, more preferably 30-38 mg/day in particular by oral administration.

In an embodiment, the daily form consists of a tablet, suppository, ampoule or other device, comprising a definitive amount of citalopram or escitalopram, the whole of which is intended to be administered as a single dose.

Throughout the description and claims the word "comprise" and variations of the word, are not intended to exclude other technical features, additives, components, or steps. Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

DETAILED DESCRIPTION

The present disclosure relates to the treatment of neurodegenerative diseases using citalopram or escitalopram as active ingrident, in particular polyglutamine diseases, in particular Machado-Joseph disease (MJD) or Spinocerebellar ataxia type 3 (SCA3).

Figure 1A:
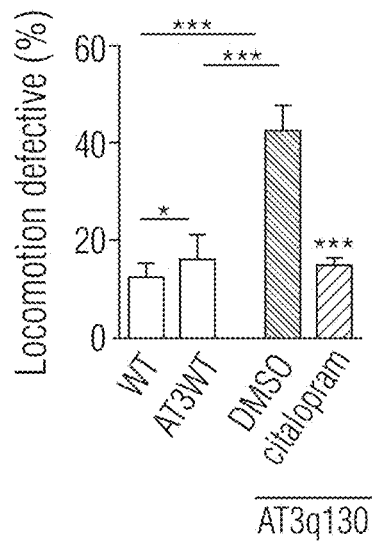
FIG. 1. Citalopram and other SSRIs restore motor performance in a *C. elegans* model of MJD. (a) Locomotion defects of AT3q130 animals upon treatment with citalopram. (b) Dose-response profile of locomotion defects of AT3q130 animals upon citalopram treatment. (c) Locomotion defects of AT3q130 animals upon treatment with S-citalopram (escitalopram), fluoxetine and zimelidine. (d) Motility performance of AT3 WT upon citalopram, S-citalopram (escitalopram) and fluoxetine treatments. (n=3±s.d.), P>0.05 (Student's t-test). AT3q130, mutant ATXN3 animals; AT3 WT, wild-type ATXN3 animals. cit, citalopram; S-cit, S-citalopram; fluox, fluoxetine; zimel, zimelidine.
Figure 1B:
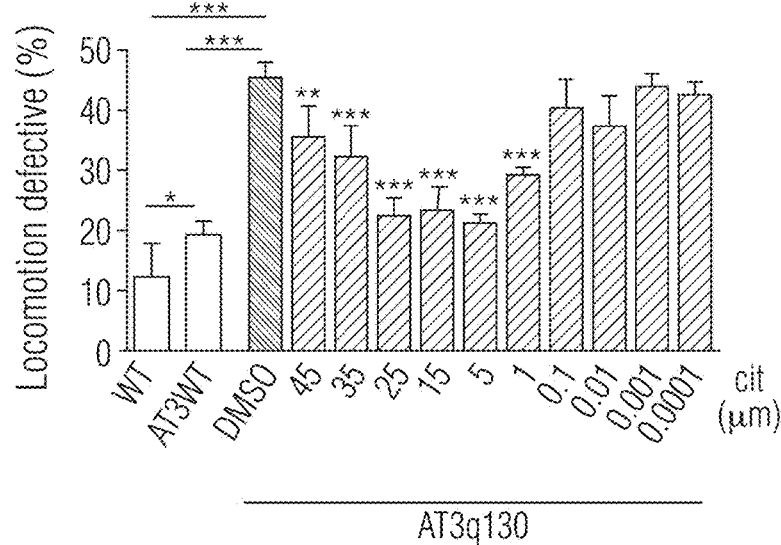
Figure 1C:
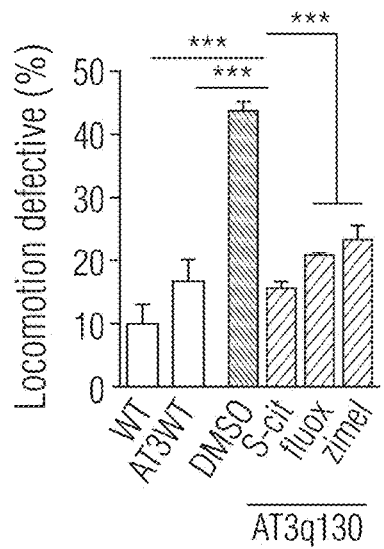
Figure 1D:
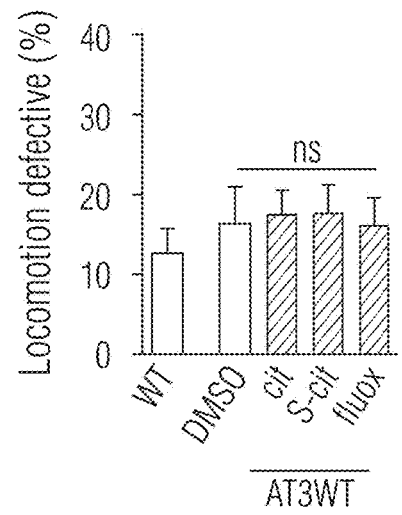
Figures 2A, 2B:
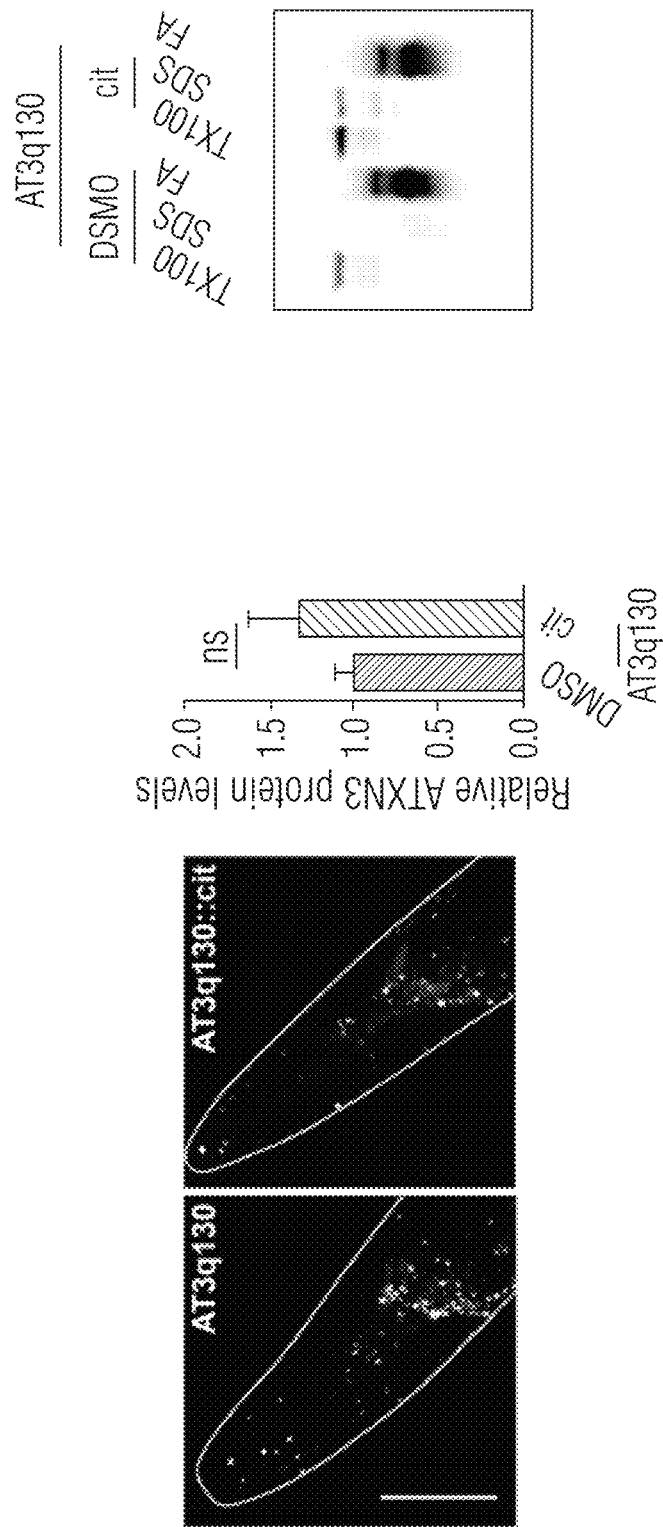
FIG. 2. Early life chronic citalopram treatment suppressed mutant ATXN3 aggregation and neuronal dysfunction in *C. elegans*. (a) Aggregate quantification in AT3q130 animals upon citalopram treatment; (b) representative Western-blot analysis of ATXN3 protein upon biochemical fractionation of AT3q130 protein extracts (out of n=3); (c) human ATXN3 protein levels in AT3q130 citalopram animals; (d) survival of AT3q130 animals upon citalopram treatment and (e) statistics; (f) motility of citalopram-treated WT and AT3q130 animals and off-drug effect as disease progressed; (g) motor behavior of AT3q130 citalopram animals treated for four days, with treatment initiation at the indicated days and (h) treatment duration for the indicated days; (i) locomotion impairment and aggregation load of AT3q130 animals in the mod-5 background and upon treatment with citalopram, S-citalopram and fluoxetine. For motor behaviour assays: (n=3-4,±s.d.), *P<0.05, P<0.01, *P<0.001 (Student's t-test). For aggregate quantification: (n≥8,±s.d.), *P<0.05, P<0.01, *P<0.001 (ANOVA, Bonferroni's test). For western-blot: (n=4,±s.d.), P>0.05 (Student's t-test). TX100, Triton X-100; FA, formic acid; cit, citalopram; S-cit, S-citalopram (escitalopram); fluox, fluoxetine; WT, wild-type.
Figures 2C, 2D:
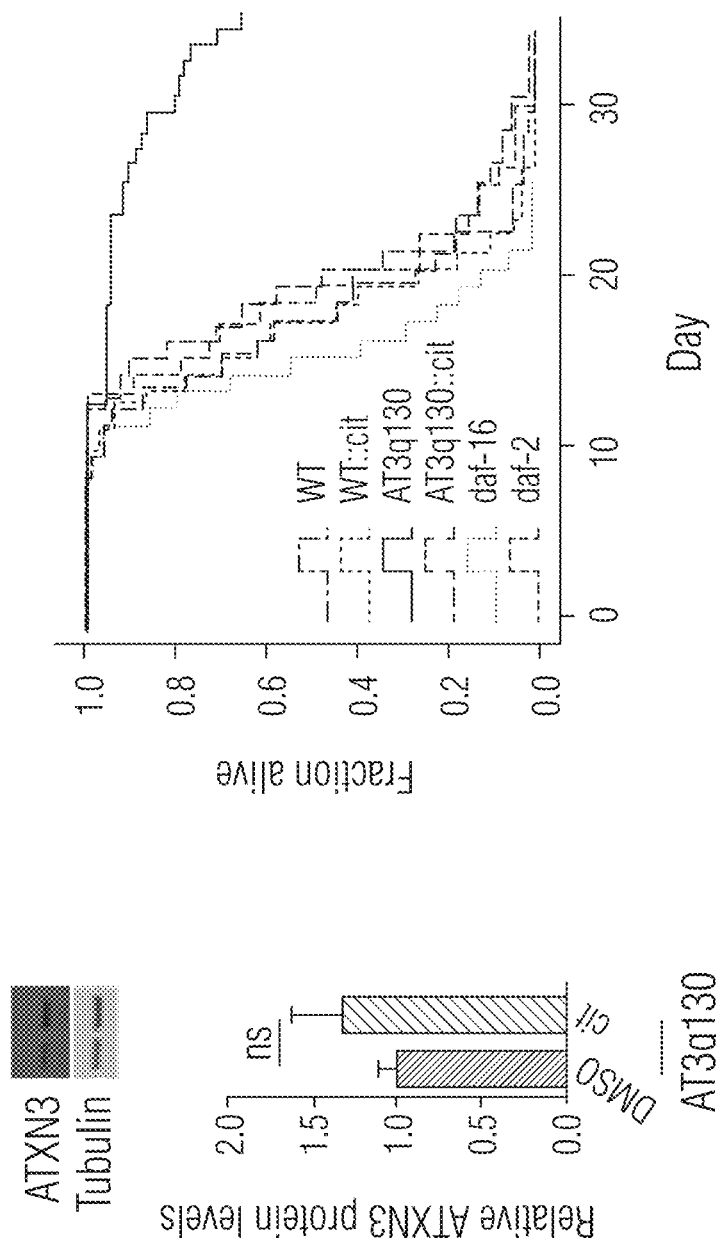

Pharmacological and Genetic Inhibition of C. elegans SERT Suppresses ATXN3 Pathogenesis Citalopram is a SSRI with a proven safety record that is widely used for treatment of depression (Mandrioli, R., Mercolini, L., Saracino, M. A. & Raggi, M. A. Selective serotonin reuptake inhibitors (SSRIs): therapeutic drug monitoring and pharmacological interactions. Curr Med Chem 19, 1846-63 (2012)). The primary molecular target of citalopram is the 5-HT transporter (SERT), which is responsible for 5-HT reuptake by serotonergic neurons. This target specificity and conservation prompted us to examine the effects of citalopram on MJD pathogenesis in an invertebrate model of the model. Treatment with citalopram caused complete rescue of mutant ATXN3-mediated neuronal dysfunction (FIG. 1a), with a dose-response profile and a derived half-maximal effective concentration ($EC_{50}$) value of 45 μM (FIG. 1b). Citalopram exists as a racemic mixture but its effects are largely due to the S-enantiomer, escitalopram; this and other SSRIs had also beneficial effects on AT3q130 animals (FIG. 1c). Normal behaviour and motility, development and fecundity in WT animals were not affected by SSRI treatment (FIG. 1d). Importantly, citalopram treatment significantly reduced mutant ATXN3 aggregation in C. elegans neurons (FIG. 2a), and increased ATXN3 solubility (FIG. 2b), as assessed by biochemical fractionation, without affecting the overall level of protein (FIG. 2c).

Figure 2F:
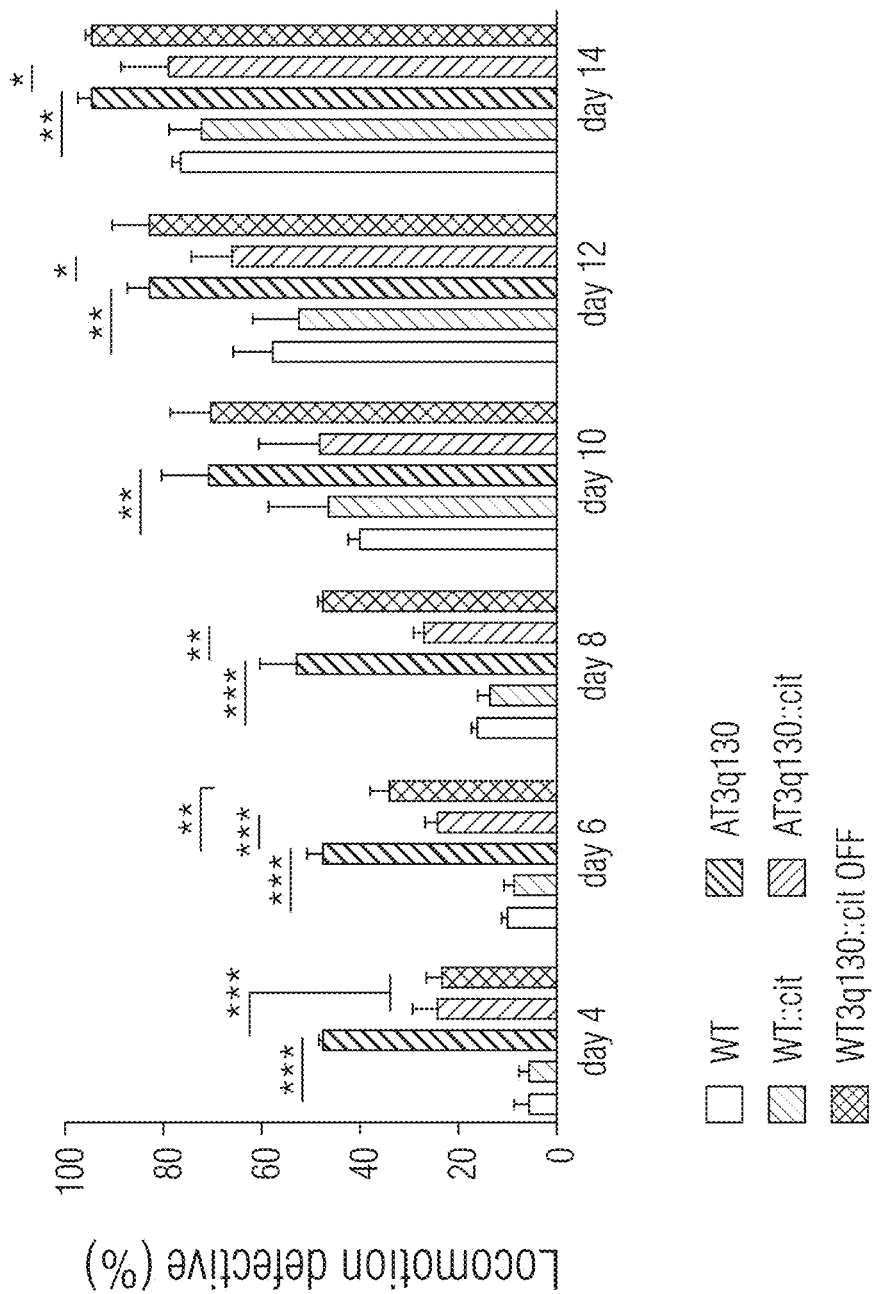
Figure 2H:
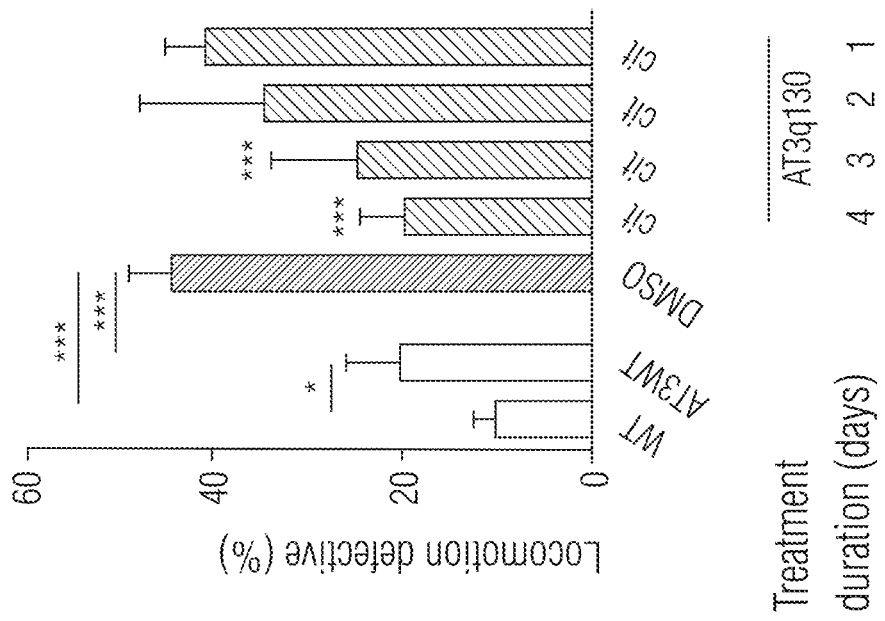
Figure 2G:
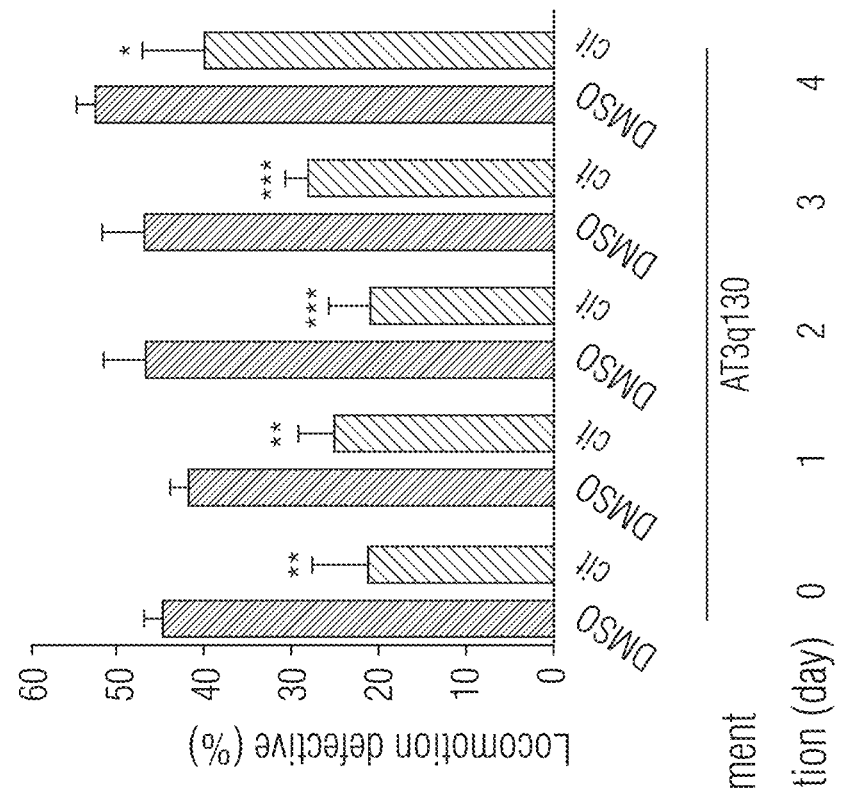

Upon continuous exposure to citalopram, the survival of AT3q130 animals was rescued (FIG. 2d, e) and neuronal dysfunction was restored in ATXN3 animals through day 14 of age (FIG. 2f). This beneficial effect declined when citalopram was withdrawn, and neurotoxicity returned after three to four days off treatment (FIG. 2f). Maximum protection required early treatment (from the egg stage through day four of adulthood) (FIG. 2g); moreover, the extent of drug exposure period was critical, as two days of treatment were insufficient to exert beneficial effects (FIG. 2h).

Figure 2I:
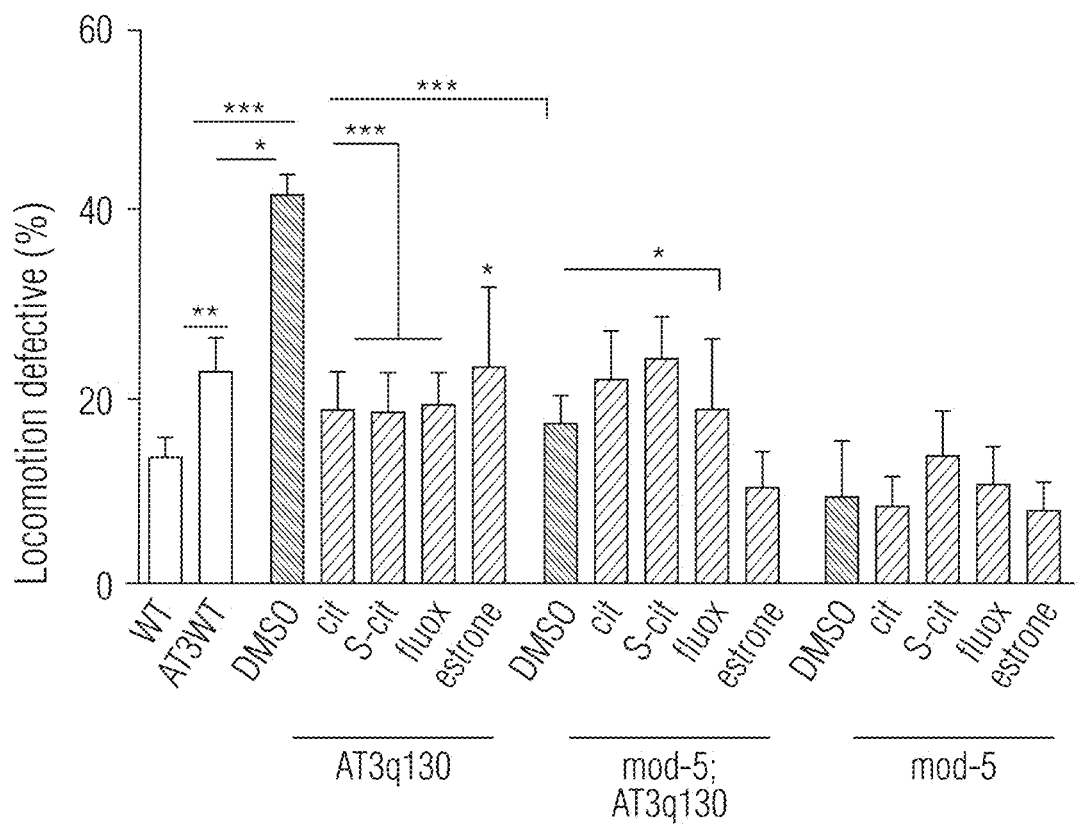
Figure 2I:
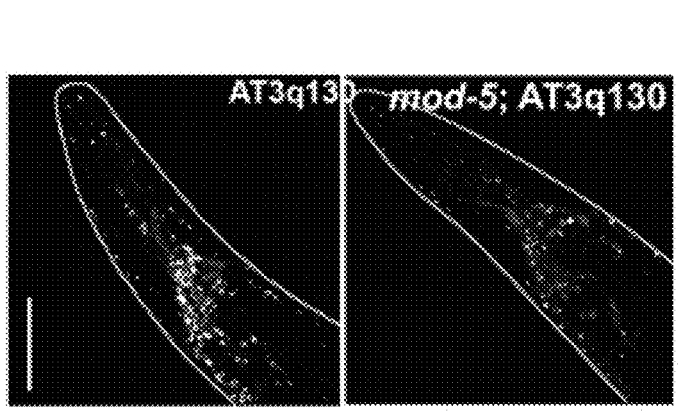
Figure 2I:
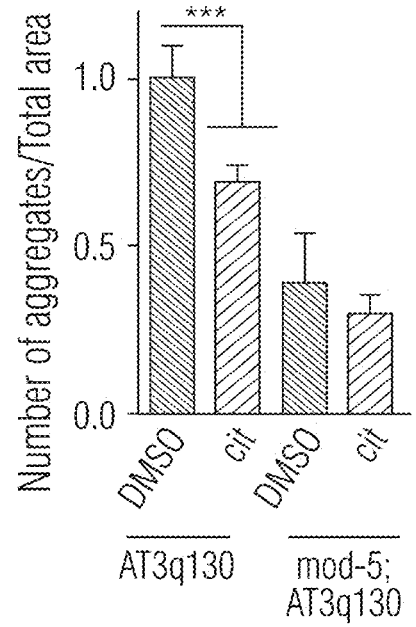

In C. elegans, there is one 5-HT transporter ortholog of the vertebrate SERT, MOD-5. To confirm the beneficial effect of pharmacological inhibition of serotonin recapture, we showed that genetic ablation of MOD-5 rescued mutant ATXN3-mediated motor dysfunction and aggregation in C. elegans (FIG. 2i). Pharmacogenetic analysis also supported MOD-5 as a cellular target of citalopram in the nematode, as treatment with this drug did not further ameliorate mutant ATXN3-mediated pathogenesis in the absence of MOD-5. In contrast, estrone (a steroid hormone) was able to further reduce the motility impairment of mod-5; AT3q130 animals (FIG. 2i), which is consistent with independent modes of action for these two compounds.

Figure 3A:
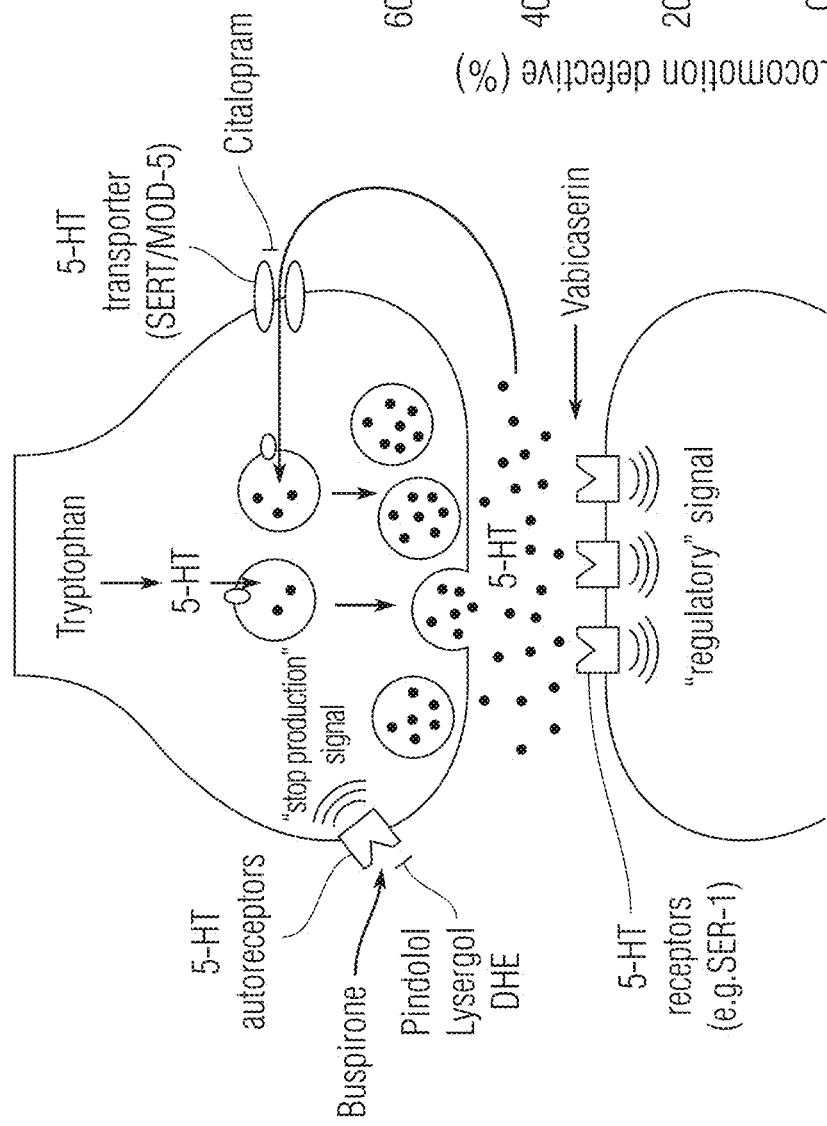
FIG. 3. Serotonergic signaling improves ATXN3 pathogenesis in a G-protein coupled receptor-dependent manner. (a) Schematic of a serotonergic synapse showing that 5-HT is synthesized and released into the synaptic cleft, where it activates post-synaptic 5-HT receptors. Vabicaserin may activate the regulatory signaling coupled with SER-1. Pindolol, lysergol and DHE probably antagonize the 5-HT autoreceptor SER-4, whereas the 5-HT1 AR agonist buspirone may desensitize the receptor, shutting-down the stop production signal mediated by 5-HT autoreceptors in pre-synaptic neurons; (b) Motor behavior of AT3q130 animals treated with vabicaserin, buspirone, DHE, pindolol and lysergol; (c) Motility defects and aggregation load of AT3q130 animals in a ser-1 genetic background, with and without citalopram, S-citalopram and estrone treatments; (d) Motility performance and mutant ATXN3 aggregation phenotypes of AT3q130 animals in the absence of SER-4. For motor behavior assays: (n=3-4,±s.d.), *P<0.05, P<0.01, *P<0.001 (Student's t-test). For aggregate quantification: (n≥12,±s. d.)*P<0.05, P<0.01, *P<0.001 (ANOVA with Bonferroni's test). DHE, dihydroergotamine; cit, citalopram; S-cit, S-citalopram (escitalopram).
Figure 3B:
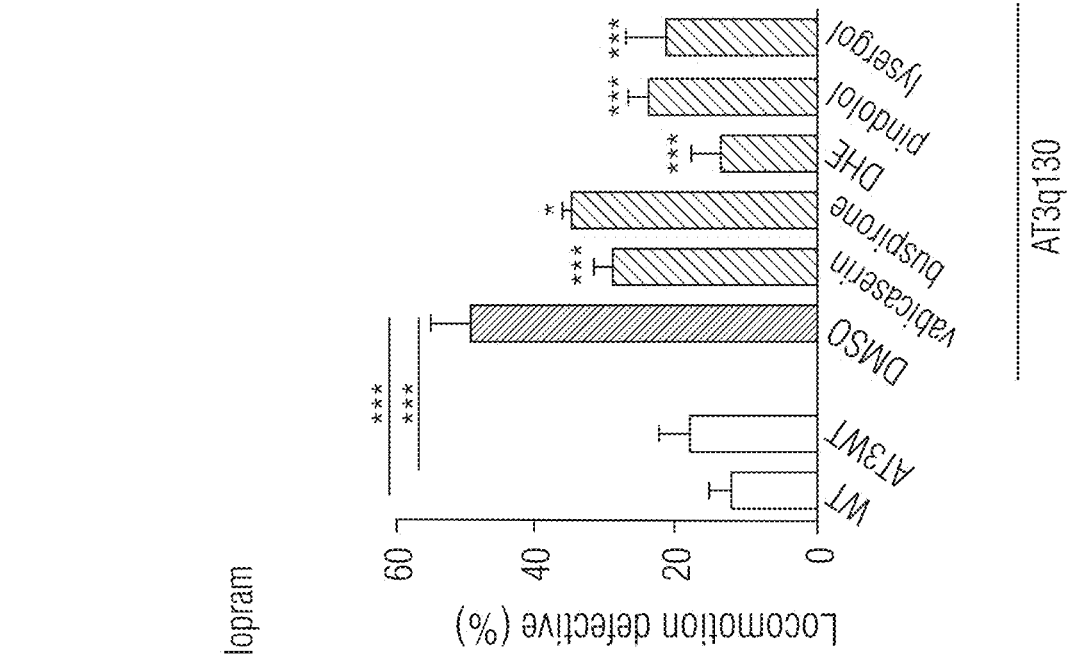
Figure 3C:
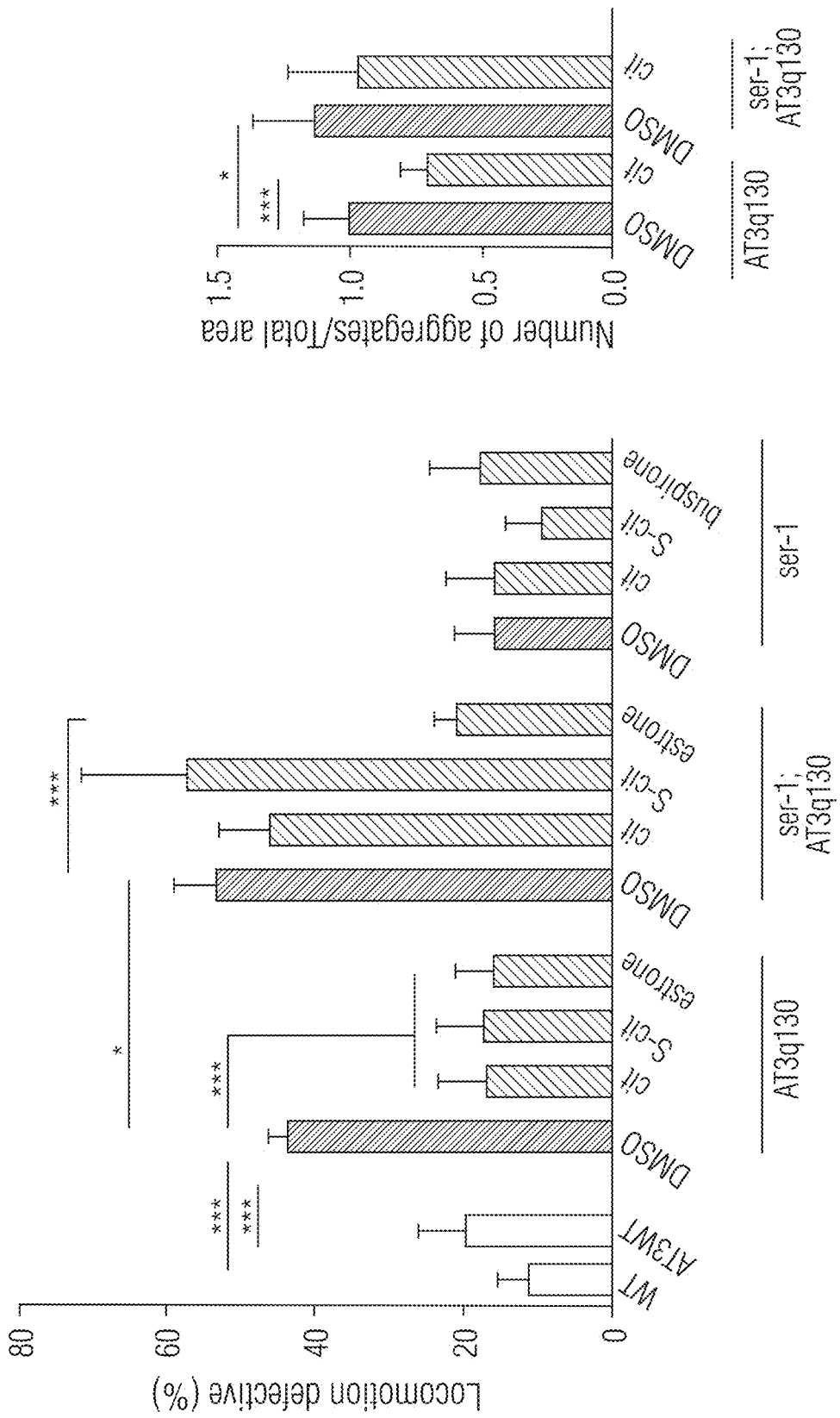
Figure 3D:
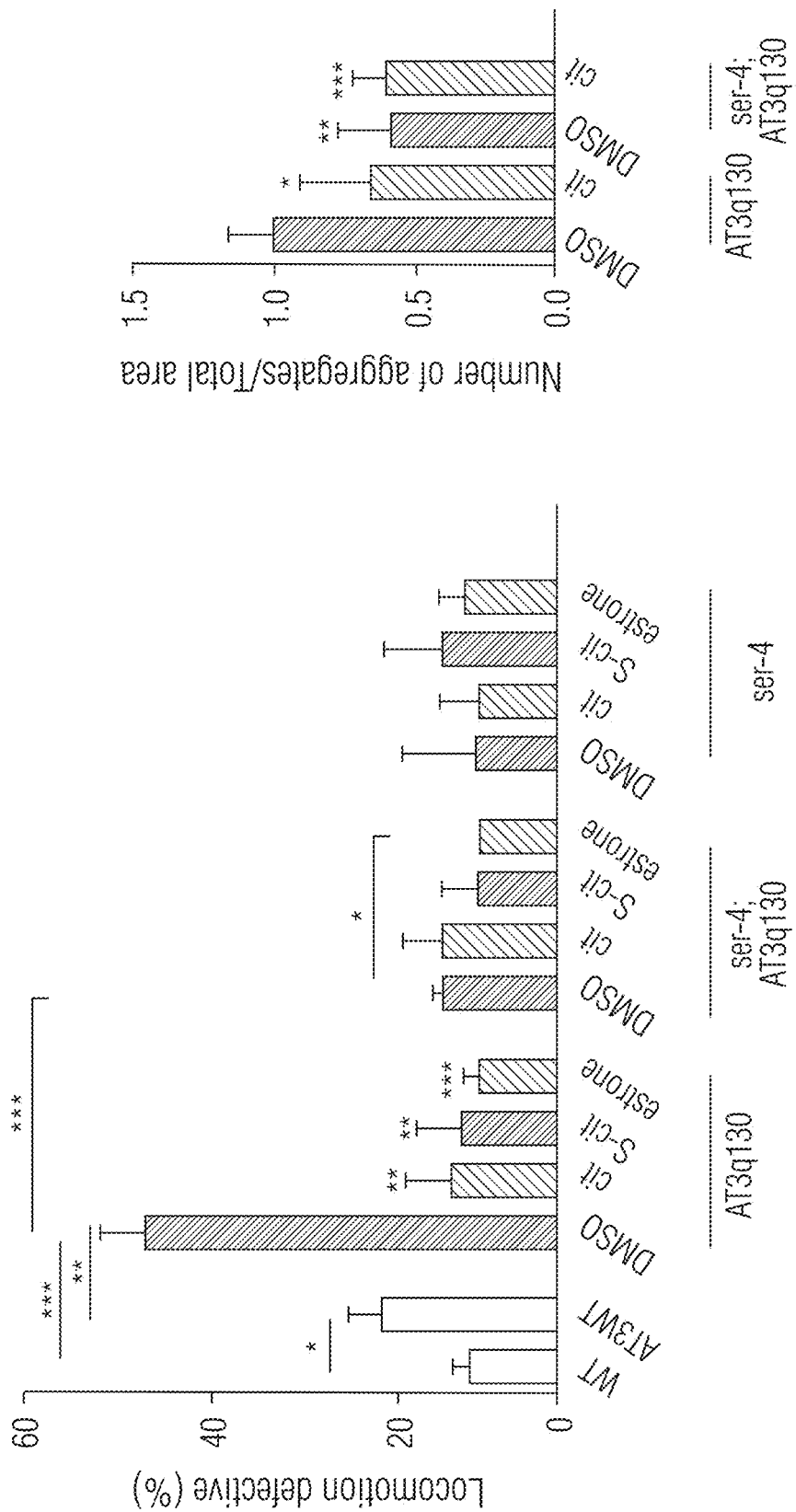

The role of 5-HT receptors (5-HTRs) was examined using pharmacological and pharmacogenetic approaches (FIG. 3a). Activation of postsynaptic 5 HTRs by the 5-HT2 CR agonist vabicaserin and stimulation of the presynaptic 5-HT autoreceptors by buspirone, dihydroergotamine, lysergol or pindolol (FIG. 3b) ameliorated mutant ATXN3-mediated motor dysfunction. Consistent with this, genetic ablation of the 5-HT post-synaptic G-protein coupled receptor SER-1 enhanced AT3q130 aggregation and locomotion defects (FIG. 3c). Likewise, the effect of citalopram was also dependent on these receptors. Additionally, ablation of the SER-4 autoreceptor, which by eliminating the negative feedback likely increases 5-HT availability, restored locomotion and reduced ATXN3 aggregation in vivo (FIG. 3d). Taken together, these results support the idea that pharmacological and genetic inhibition of MOD-5 restores motility and suppresses aggregation of AT3q130 through modulation of 5 HTR activity.

Citalopram Treatment Improves Motor Balance and Coordination of CMVMJD135 Mice

Figure 4A:
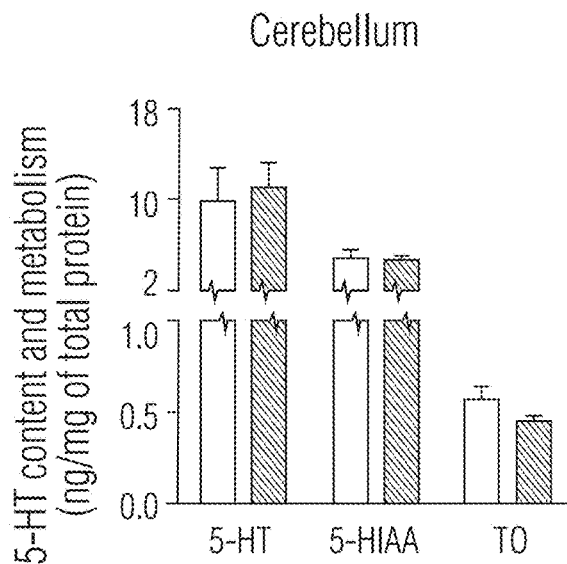
FIG. 4. CMVMJD135 mice show normal levels of 5-HT and 5-HT metabolic turnover at fully symptomatic stages of disease. Levels of 5-HT, 5-hydroxyindoleacetic Acid (5-HIAA) and 5-HT turnover (assessed by the 5-HIAA/5-HT ratio) were measured by HPLC (a) in the cerebellum (n=5 WT; n=7 CMVMJD135), (b) medulla oblongata (n=6 WT; n=8 CMVMJD135) and (c) substantia nigra (n=5 WT; n=5 CMVMJD135) at 24 weeks of age. Data presented as the mean±s.e.m. P>0.05 (Student's t-test). TO, turnover. WT, wild-type.
Figure 4B:
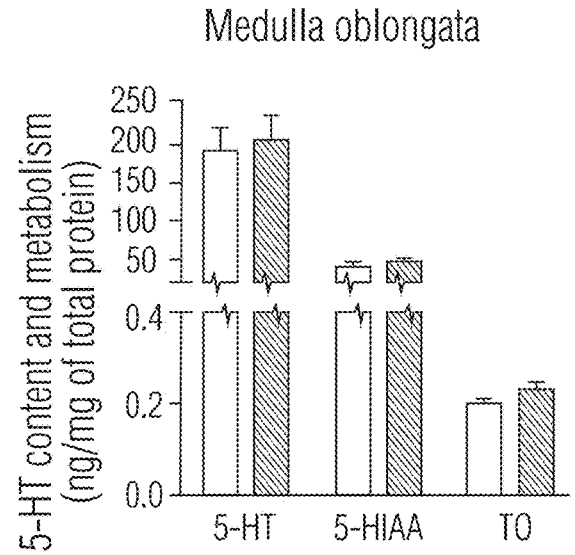
Figure 4C:
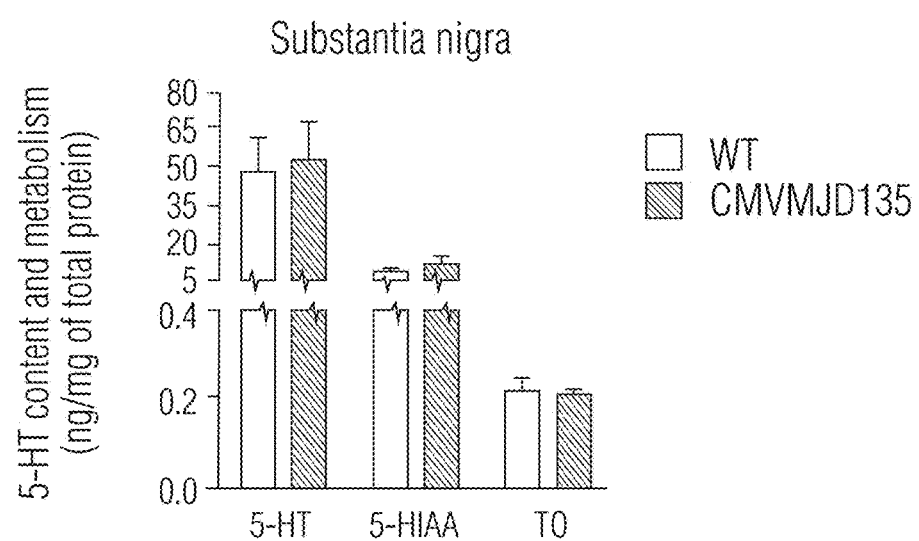
Figure 5A:
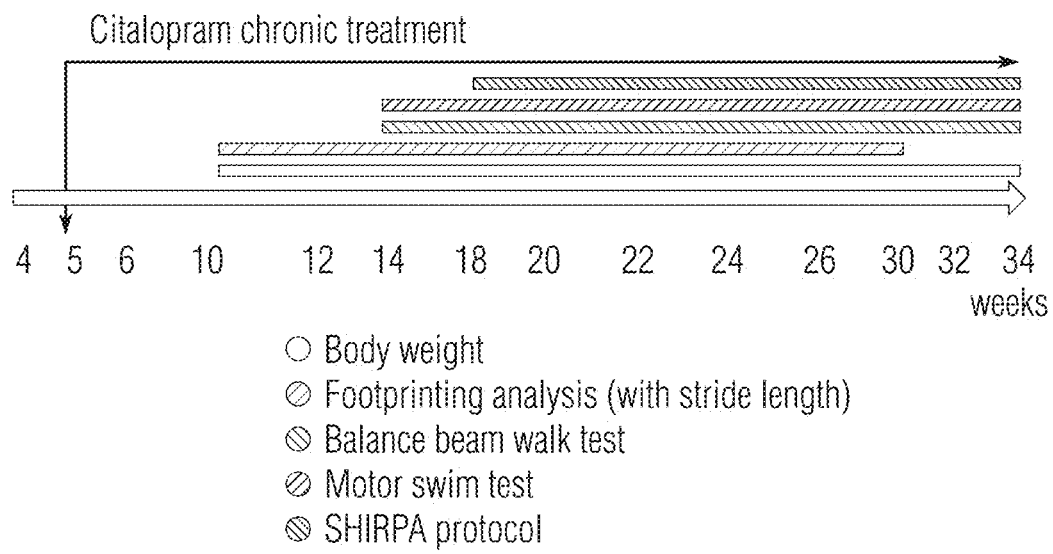
FIG. 5. Impact of citalopram treatment at 8 mg/kg on the neurological deficits of CMVMJD135 mice. (a) Schematic representation of the pre-clinical therapeutic trial. (b) Significant differences were observed between vehicle (n=13) and citalopram treated CMVMJD135 mice (n=16) in body weight (P=0.001, 20-34 weeks); (c) Mild improvement in the dragging of the paws at 14 weeks of age. (d) No improvement in exploratory activity. (e) No effect on muscle strength tests: hanging wire and forelimb strength, and on (f) hindlimb tonus. (g) Significant differences were observed between vehicle (n=13) and citalopram treated CMVMJD135 mice (n=16) in stride length (P=0.015, 30 weeks). (h) Tremors, (i) limb clasping and (j) gait were evaluated from 18 to 34 weeks of age with phenotype amelioration at late stages. (n=13-16,±s.d.), *P<0.05, P<0.01 and *P<0.001 (Mann-Whitney U test for non-parametric variables and ANOVA, Tukey correction for continuous variables. For hanging wire test: R squares comparison of the logarithmic model for CMVMJD135 groups). cit, citalopram.
Figure 5B:
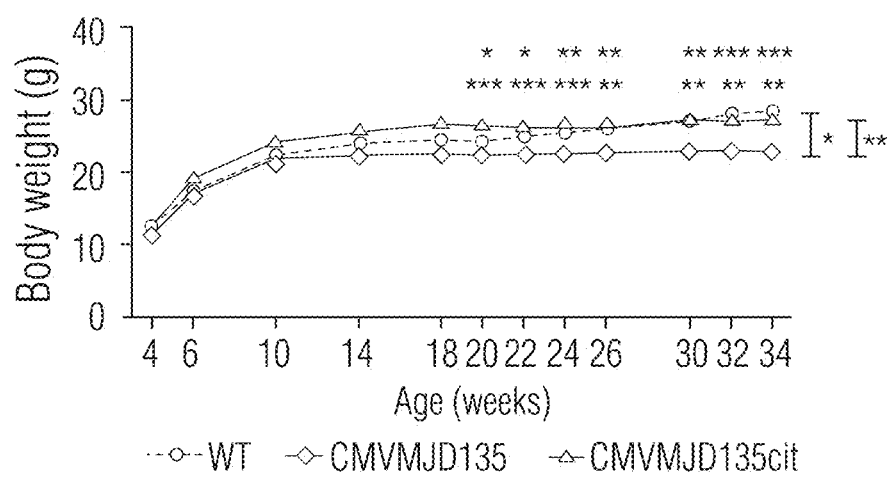
Figure 5C:
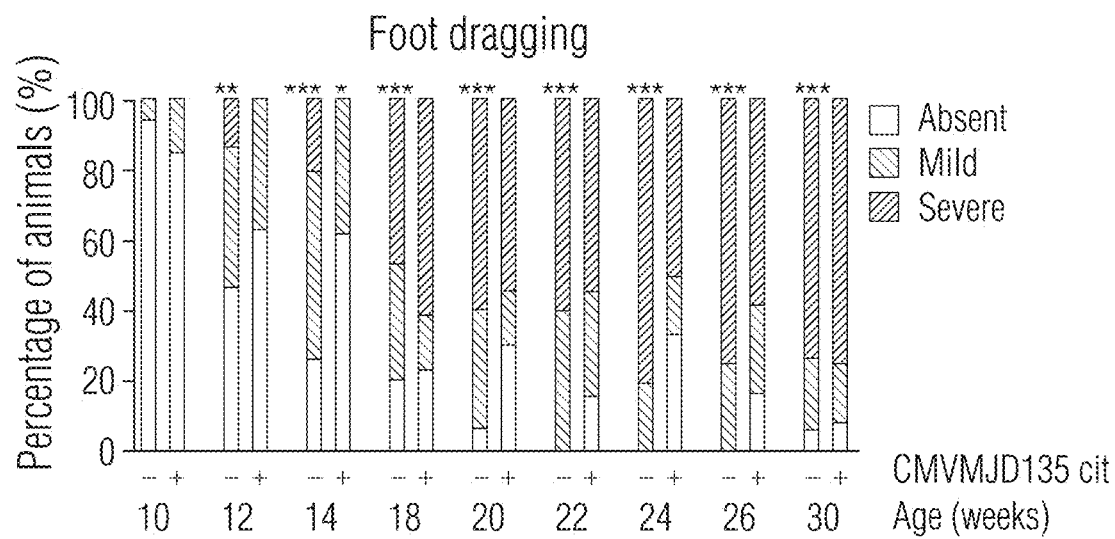
Figure 5D:
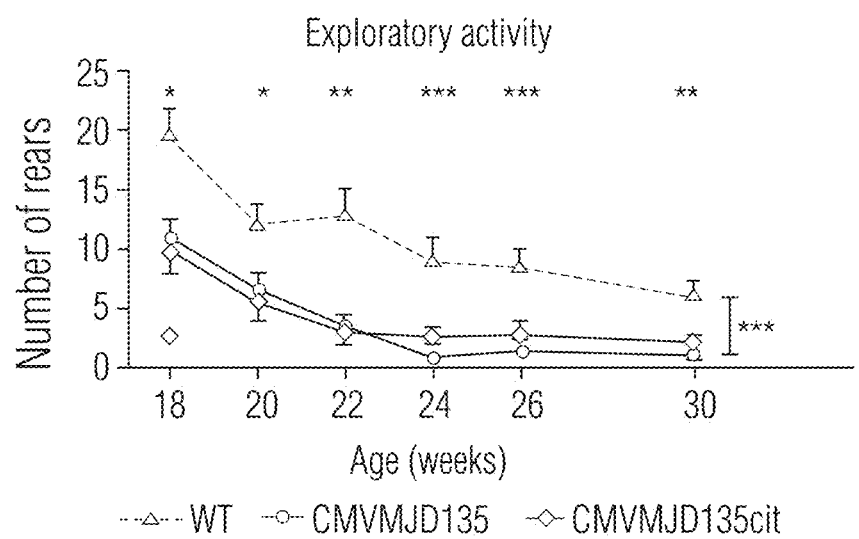
Figure 5E:
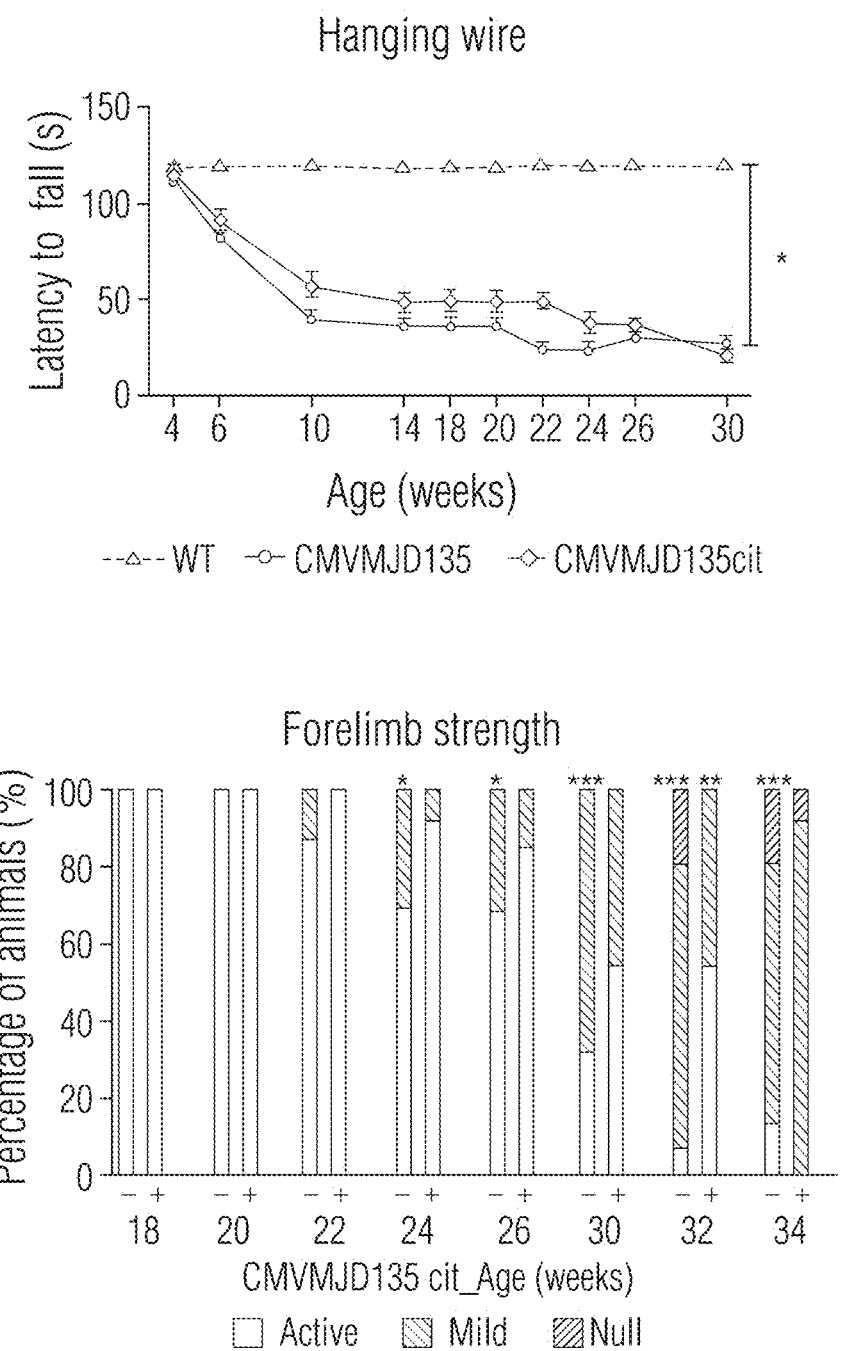
Figure 5F:
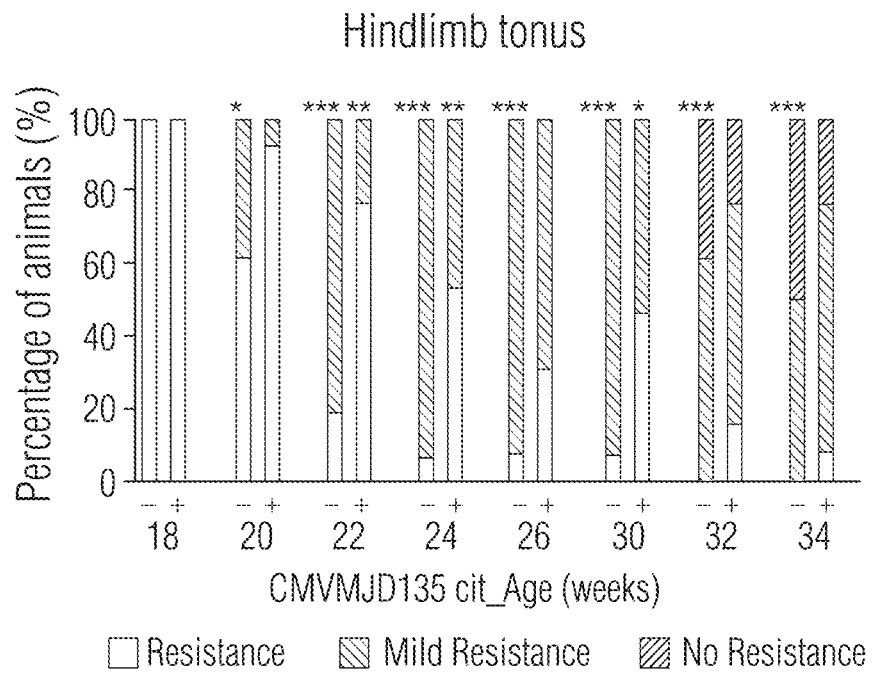
Figure 5G:
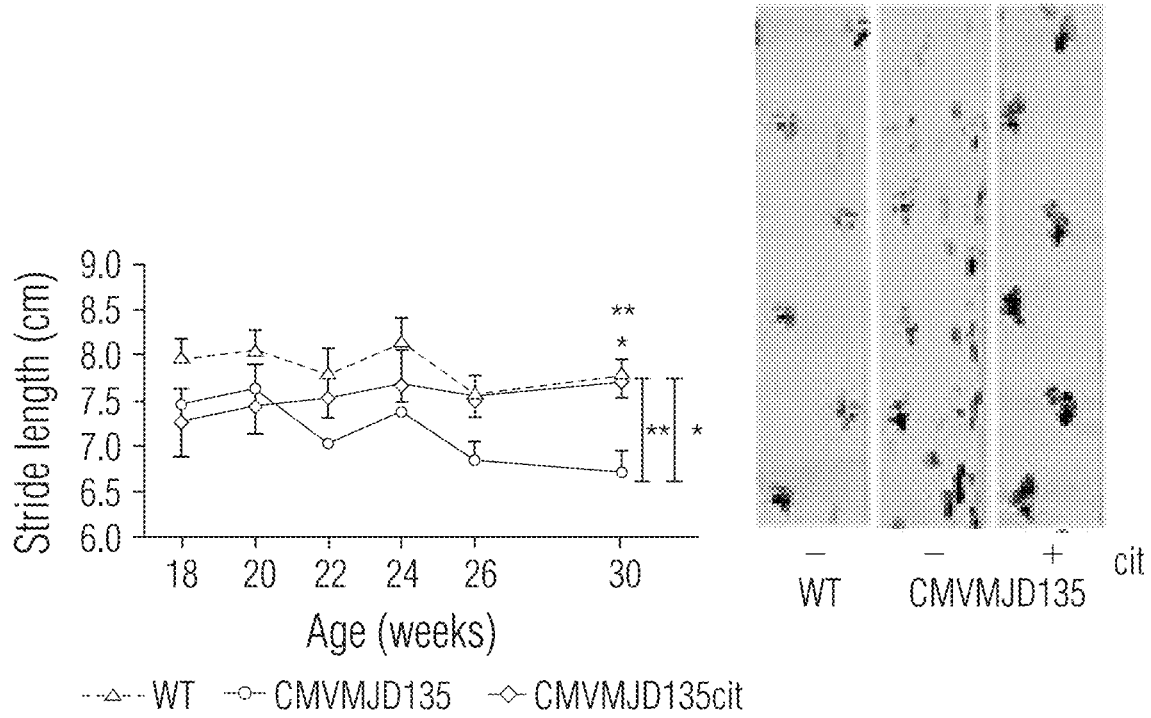
Figure 5H:
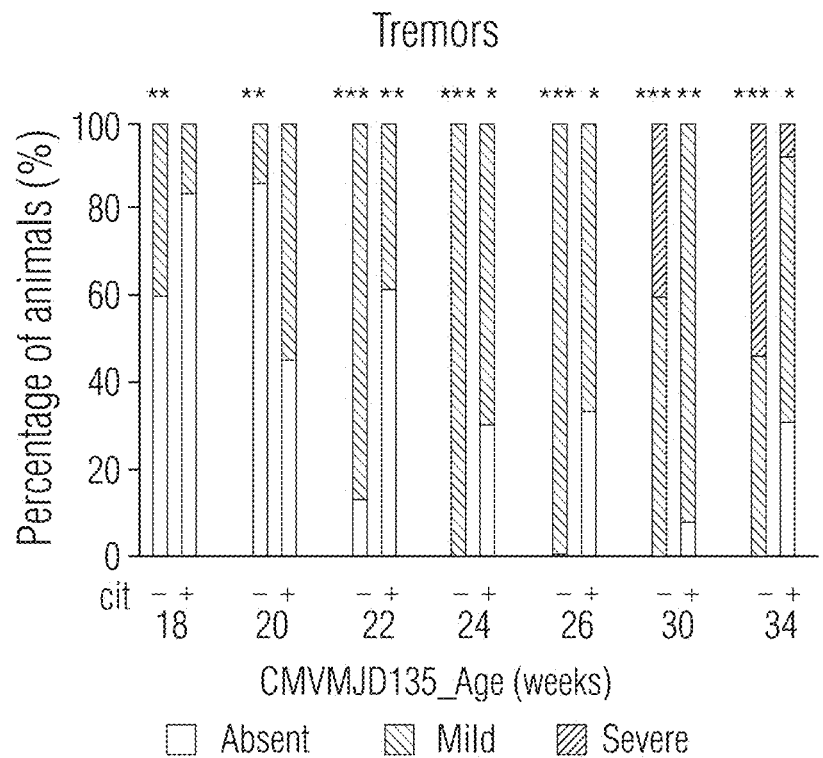
Figure 5I:
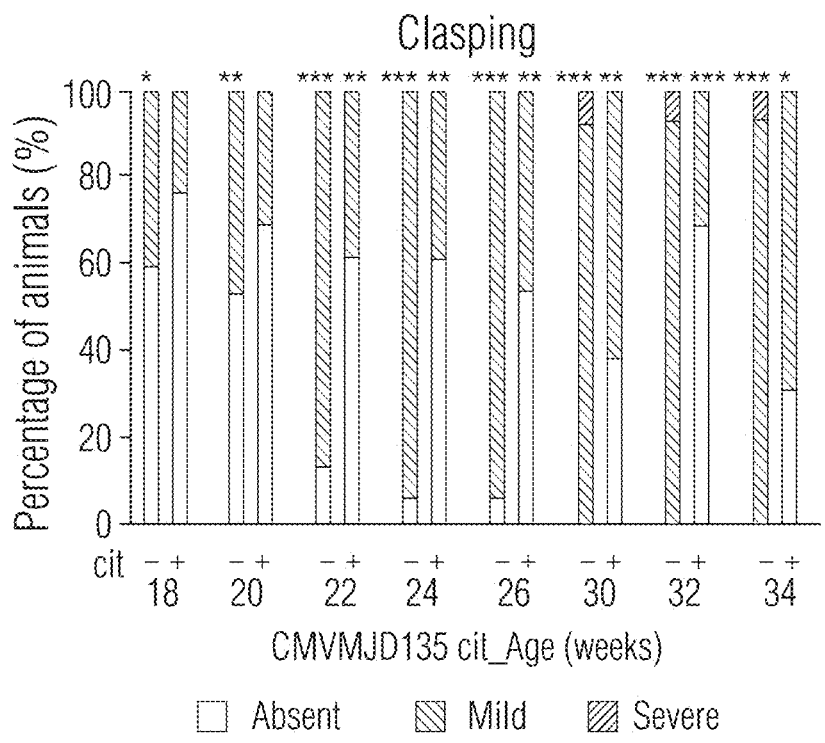
Figure 5J:
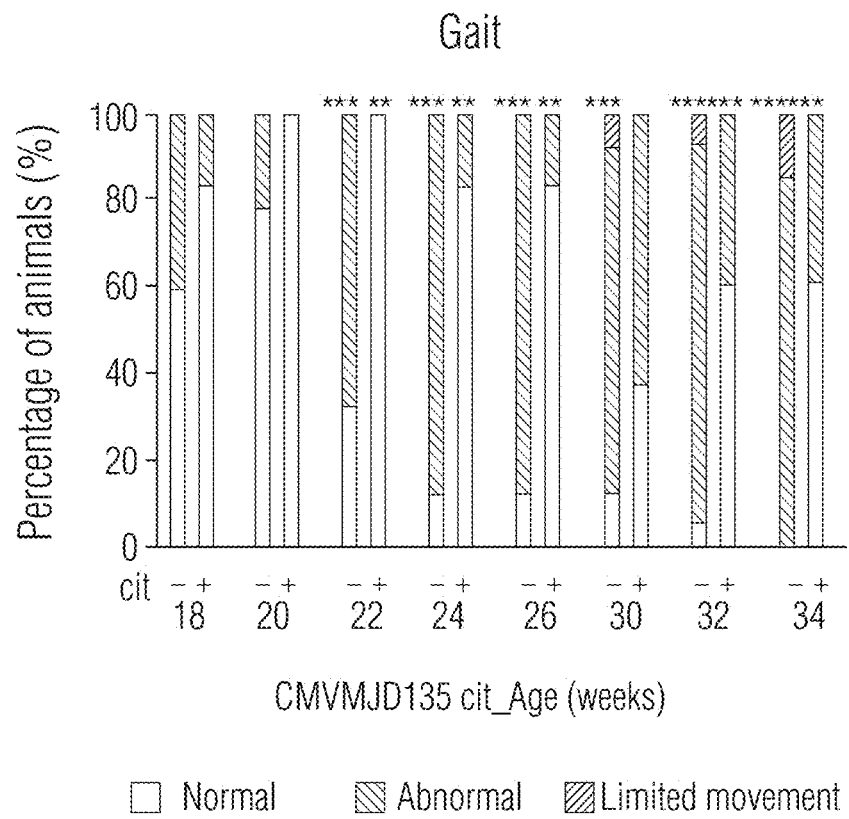
Figure 6A:
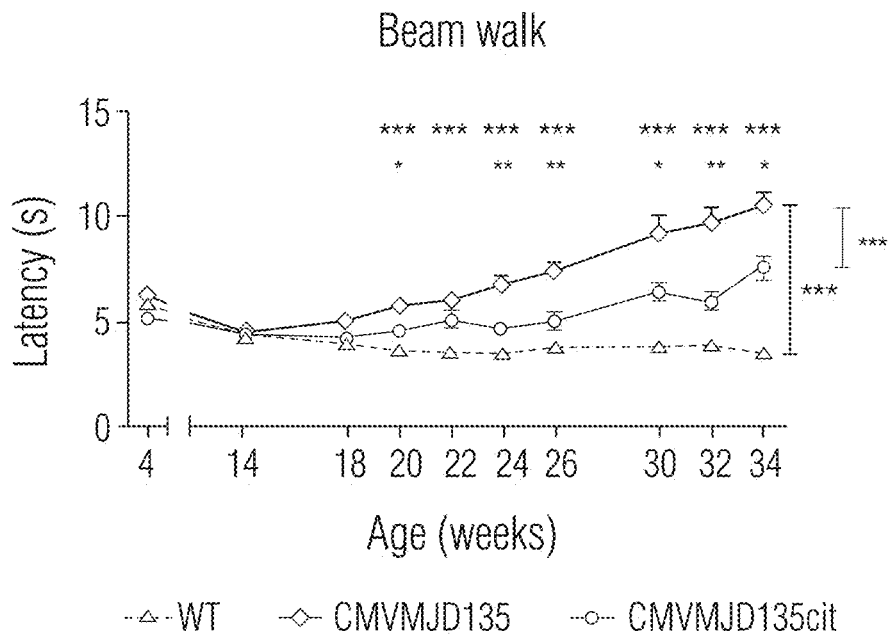
FIG. 6. Citalopram treatment attenuates impairments in balance and coordination, as well as mutant ATXN3 aggregation in MJD mice. Significant differences observed between vehicle (n=13) and citalopram treated CMVMJD135 mice (n=16) in (a) balance beam walk test (P<0.001, 20-34 weeks) and (b) swimming (P<0.001, 14-34 weeks) tests; (c) Immunohistochemistry and quantification of GFAP-positive cells per area in SN from WT, vehicle and citalopram treated CMVMJD135 mice (n=5 per group). (d) Neuronal inclusions in the PN, RtTg, 7N and LRt of vehicle and cit treated CMVMJD135 mice (n=4, 34 weeks); (e) Brainstem immunoblots and quantification of total human ATXN3 protein from vehicle and cit treated CMVMJD135 mice (n=5, 34 weeks). Data presented as mean±s.e.m., *P<0.05 and **P<0.01 (ANOVA, Tukey correction (a, b) and One-way ANOVA (c-e)). Scale bars, 20 μm. cit, citalopram; WT, wild-type; SN, substantia nigra; PN, pontine nuclei; RtTg, reticulotegmental nuclei of pons; 7N, facial motor nuclei; LRt, lateral reticular nuclei.
Figure 6B:
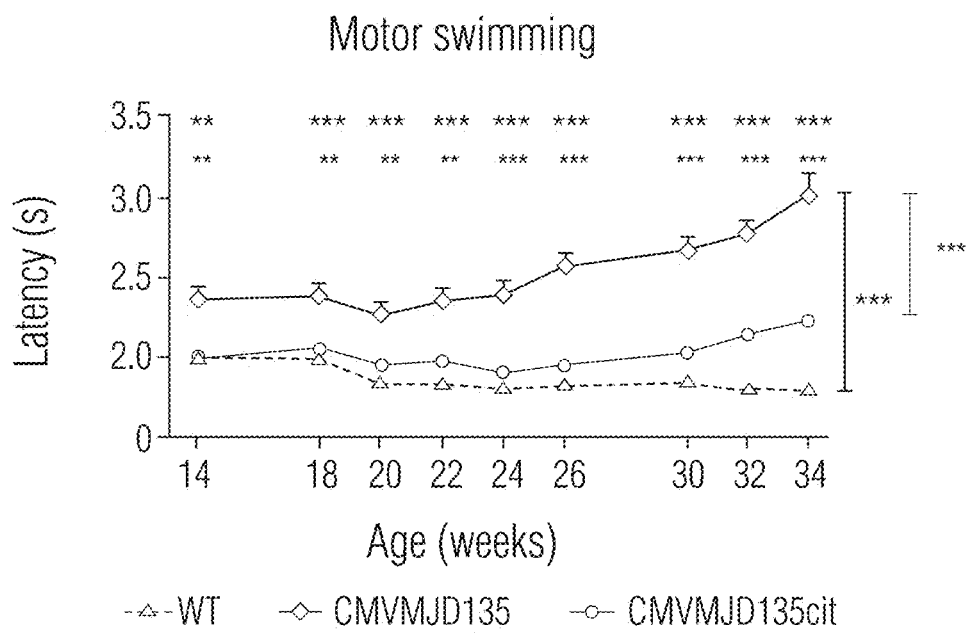

To further demonstrate the therapeutic effect of citalopram, we used a transgenic mouse model of MJD, CMVMJD135, which displays progressive MJD-like motor decline and neuropathology, including ATXN3-positive intranuclear inclusions in the central nervous system (CNS). Although CMVMJD135 mice showed no changes in baseline 5-HT levels measured by HPLC (FIG. 4), oral administration of citalopram (8 mg/kg) to these animals (study design-FIG. 5a) prevented their decreased body weight gain (FIG. 5b) and had significant beneficial effects on the motor phenotype. While there was only marginal improvement in the dragging of the paws (FIG. 5c) and limited effects on exploratory activity (FIG. 5d), strength to grab (FIG. 5e) and hindlimb tonus (FIG. 5f), citalopram treatment restored stride length to WT levels at advanced stages of the trial (FIG. 5g). Moreover, treated animals showed reduced tremors (FIG. 5h), reduced limb clasping (FIG. 5i), and improved gait quality (FIG. 5j). Citalopram treatment also resulted in a striking improvement in balance and motor coordination as compared to vehicle-treated CMVMJD135 mice. In the balance beam walk test, we observed major improvements in the time taken to cross a 12 mm square beam from 20 to 34 weeks of age (FIG. 6a). The most remarkable benefits of citalopram were observed in the motor swimming test (FIG. 6b), since at many time points and until quite late in the trial citalopram treated animals were indistinguishable from WT. Overall, these results demonstrate that citalopram can reduce the impairment in motor coordination of the MJD mouse, with less benefit on strength, suggesting effects at the level of the brainstem, midbrain or cerebellum, rather than on spinocerebellar tracts and muscle innervation. Treatment also significantly delayed disease progression in mice.

Figure 7A:
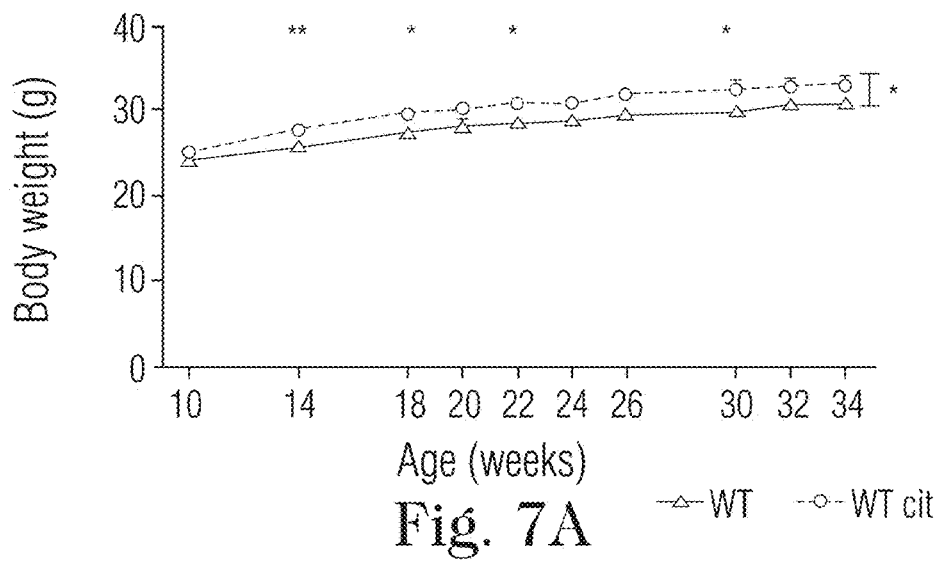
FIG. 7. Impact of citalopram treatment at 8 mg/kg on body weight and on motor behaviour of WT mice. (a) Body weight, (b) beam walk and (c) motor swimming tests of vehicle and citalopram treated WT mice. Citalopram treatment resulted in a significant increase in body weight (Treatment: $F_{1, 18}$=5.337, P=0.033). No differences between WT and citalopram treated WT mice were observed in the beam walk (Treatment: $F_{1, 16}$=0.748, P=0.40) and motor swimming tests (Treatment: $F_{1, 14}$=0.043, P=0.839). (n=10±s.e.m.), *P<0.05, P<0.01 and *P<0.001 (Repeated-measures ANOVA). cit, citalopram; WT, wild-type.
Figure 7B:
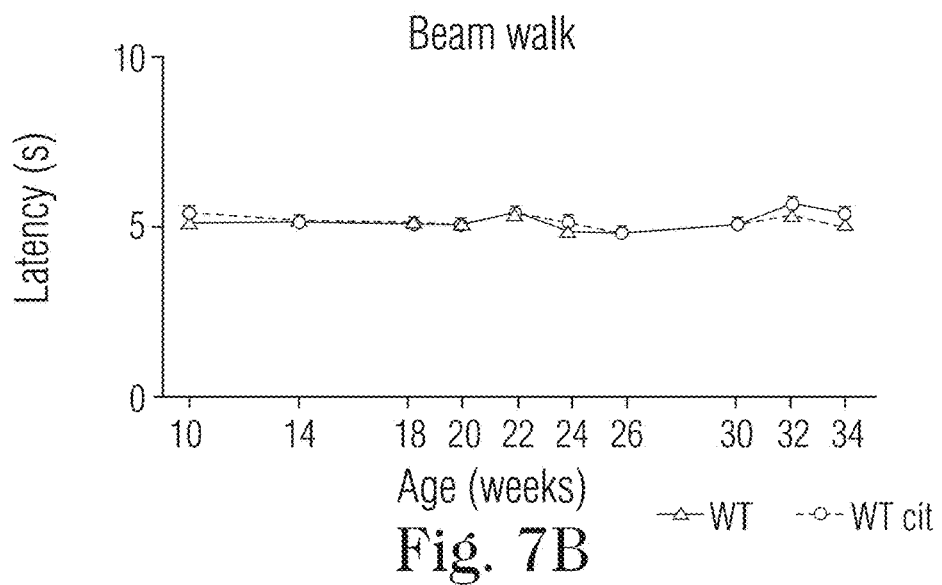
Figure 7C:
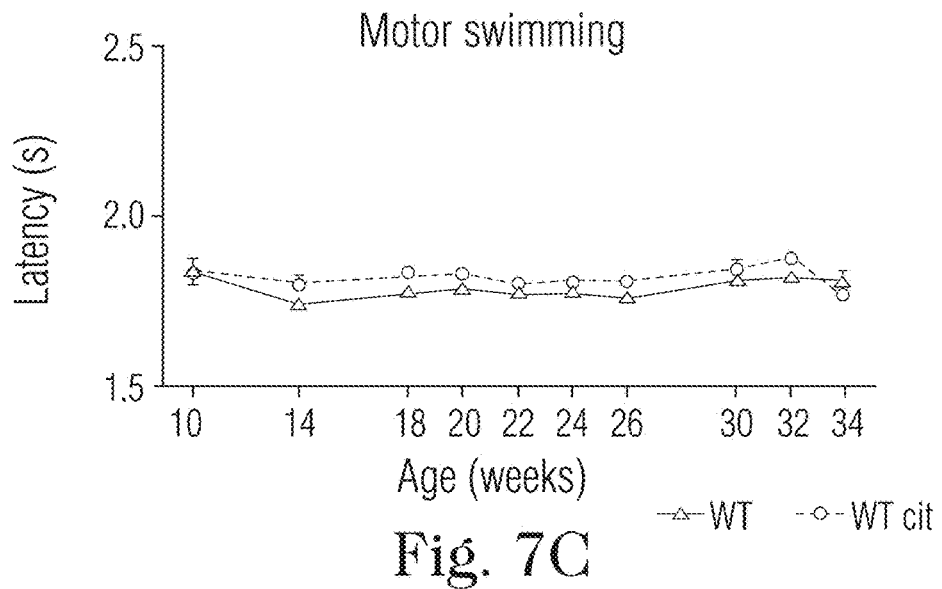
Figure 8A:
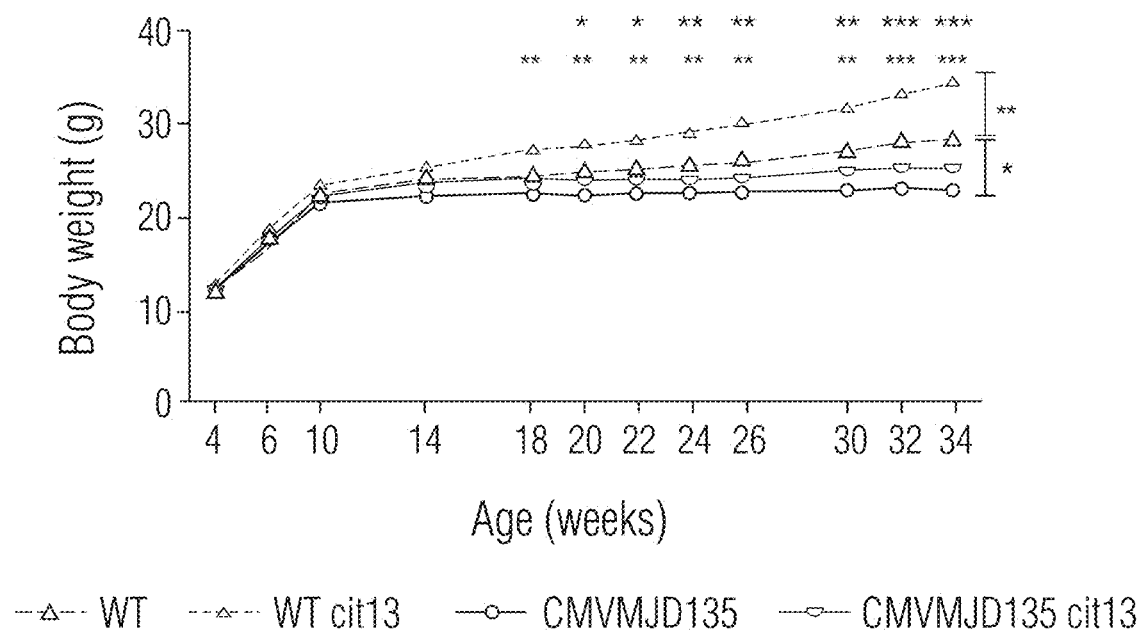
FIG. 8. Treatment with a higher dosage of citalopram (13 mg/kg) led to a limited improvement of neurological symptoms of CMVMJD135 mice. (a) Body weight, (b) stride length, (c) beam walk and (d) motor swimming tests of vehicle (n=14) and citalopram treated (13 mg/kg) WT (WT cit 13) mice (n=17) and of vehicle (n=16) and citalopram treated (13 mg/kg) CMVMJD135 mice (CMVMJD135 cit 13) (n=13). No differences were observed in body weight between CMVMJD135 and CMVMJD135 cit 13 mice (Genotype: $F_{1, 67}$=31.335, P<0.001; Treatment: $F_{2, 67}$=14.181, P=0.000007; Genotype*Treatment $F_{1, 67}$=1.425, P=0.237; Post-hoc Tukey test (vehicle versus cit treated CMVMJD135 mice, P=0.431). Citalopram treated WT mice showed a significant increase in body weight (Tukey test, P=0.007). No differences were observed in stride length upon treatment. Regarding the balance beam walk test, a marginal amelioration of performance was detected at 20 and 24 weeks of age (One-way ANOVA, Tukey test, P=0.03 and P=0.031, respectively; Genotype: $F_{1, 49}$=124.181, P<0.001; Treatment: $F_{1, 49}$=2.478, Genotype*Treatment: $F_{1, 49}$=2.478, P=0.122). In the motor swimming test, significant differences upon treatment were observed only at 22 and 34 weeks of age (One-way ANOVA, Tukey test, P=0.016 and P=0.041, respectively, Genotype: $F_{1, 64}$=118.157, P<0.001, Treatment: $F_{2,64}$=19.959, P<0.001; Genotype*Treatment: $F_{1, 64}$=6.3, P=0.015). Data presented as mean±s.e.m., *P<0.05, P<0.01 and *P<0.001 (Repeated-measures ANOVA, Tukey correction). cit 13, citalopram at 13 mg/kg; WT, wild-type.
Figure 8B:
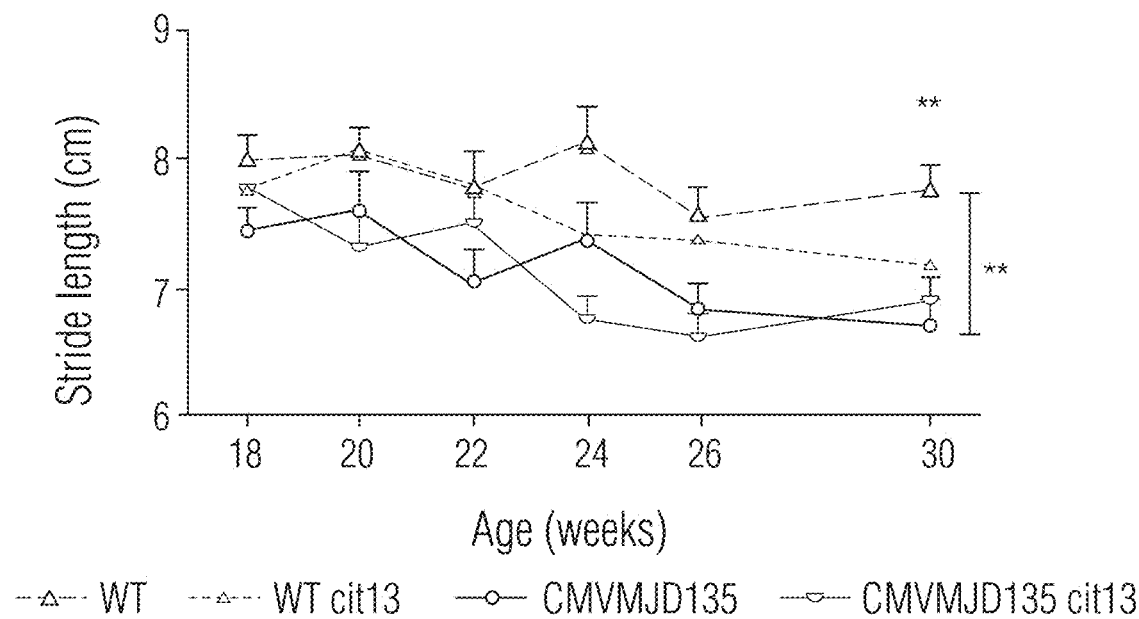
Figure 8C:
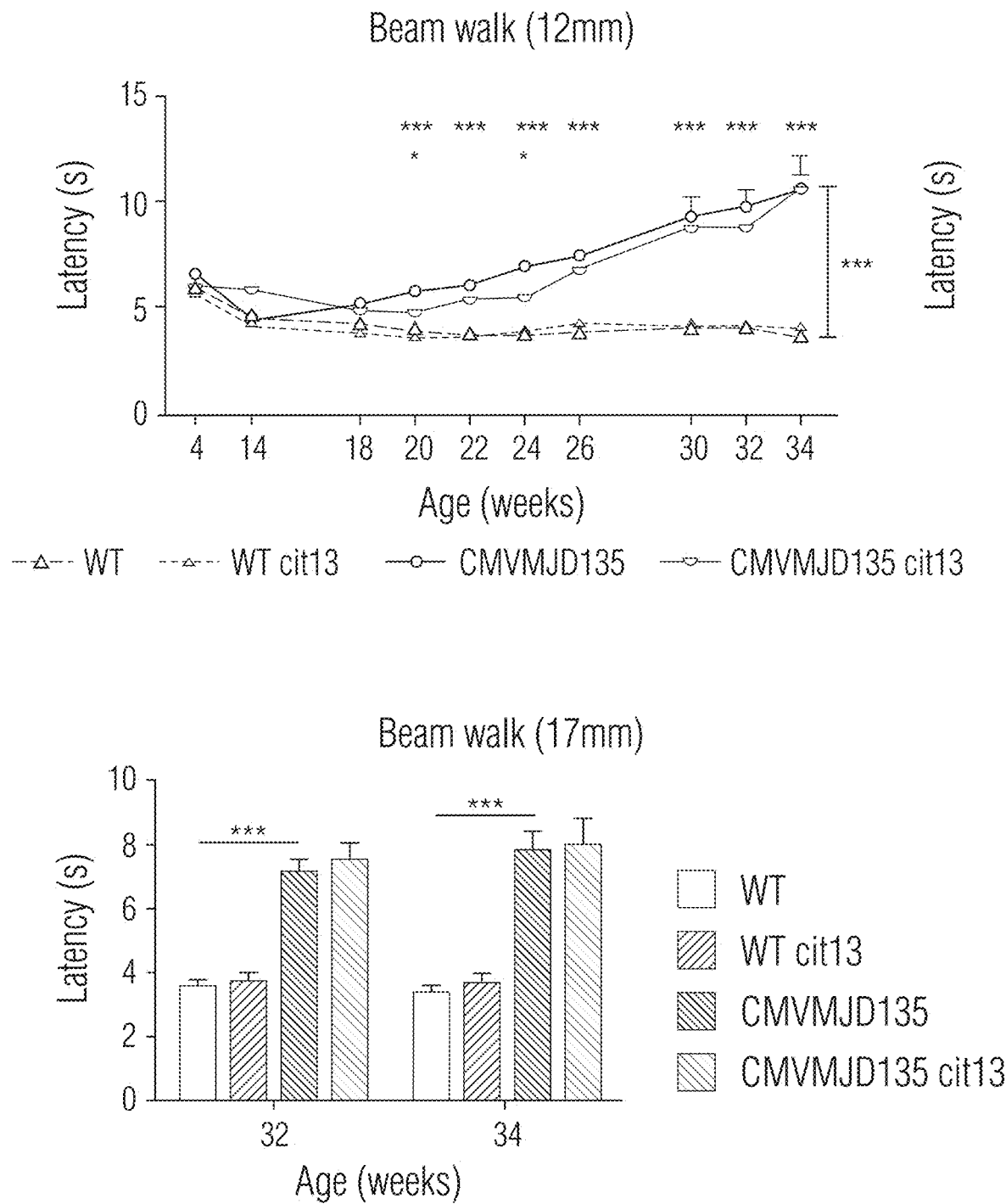
Figure 8D:
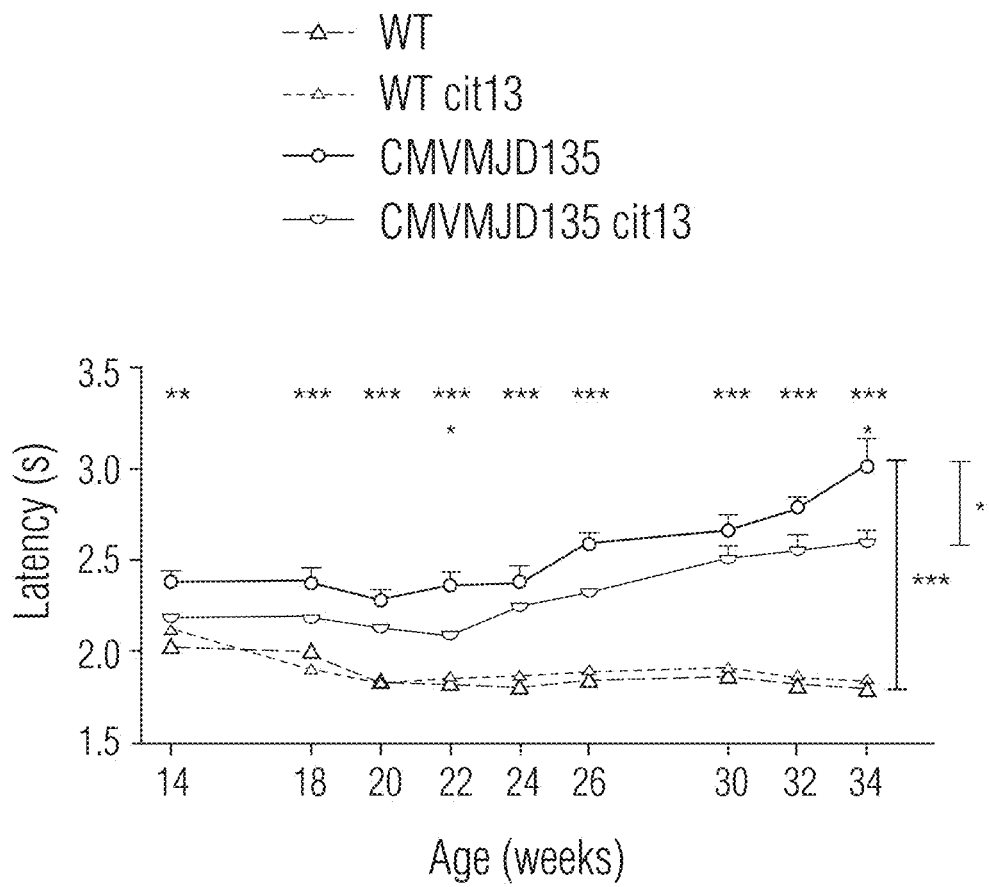

In an embodiment, citalopram treated WT mice behaved similarly to their untreated littermates, confirming the specificity of the effect (FIG. 7). Moreover, CMVMJD135 mice treated with a dosage of 13 mg/kg showed more limited improvements when compared to vehicle treated controls in all paradigms mentioned above (FIG. 8).

Figure 6C:
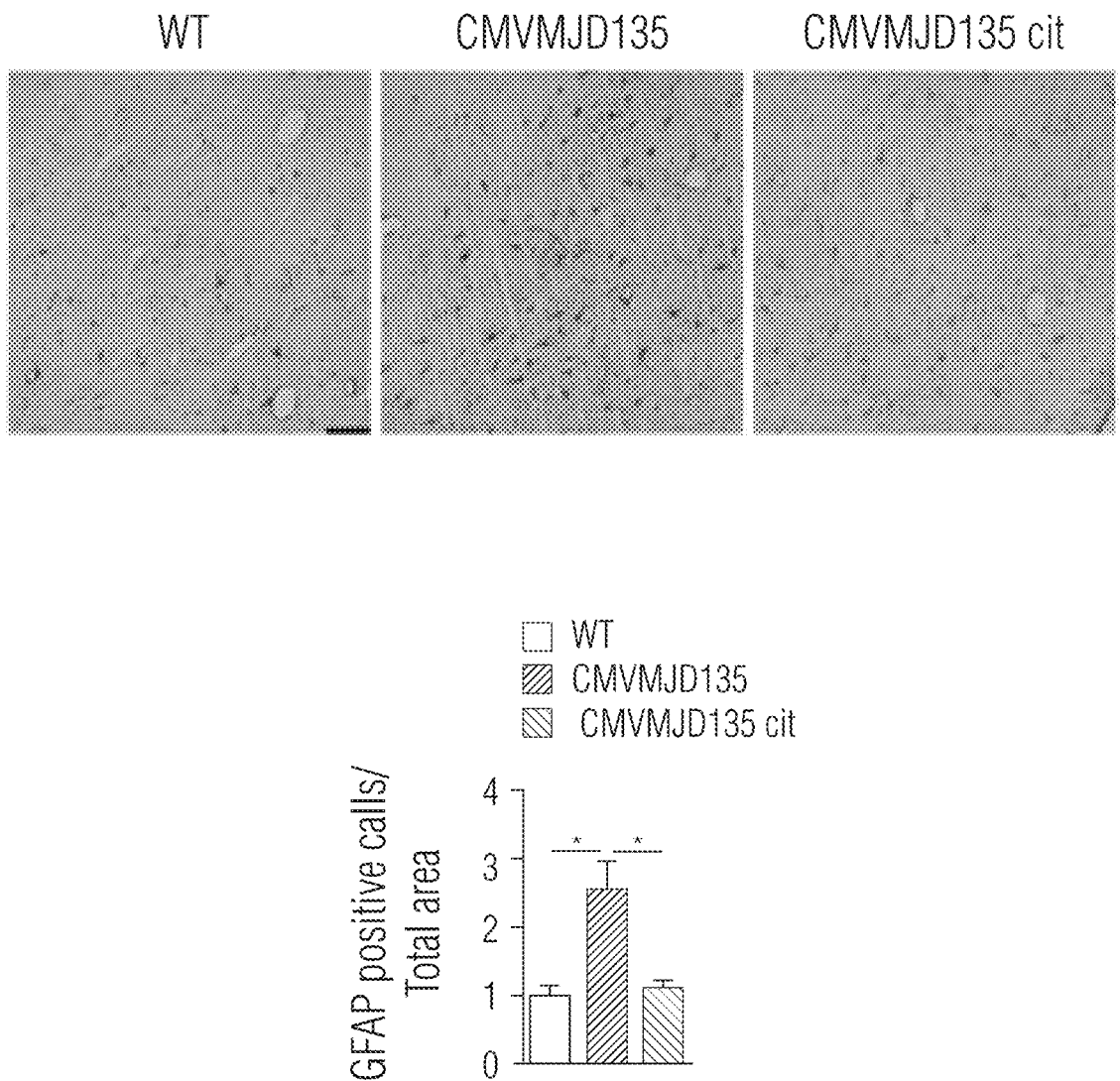
Figure 6D:
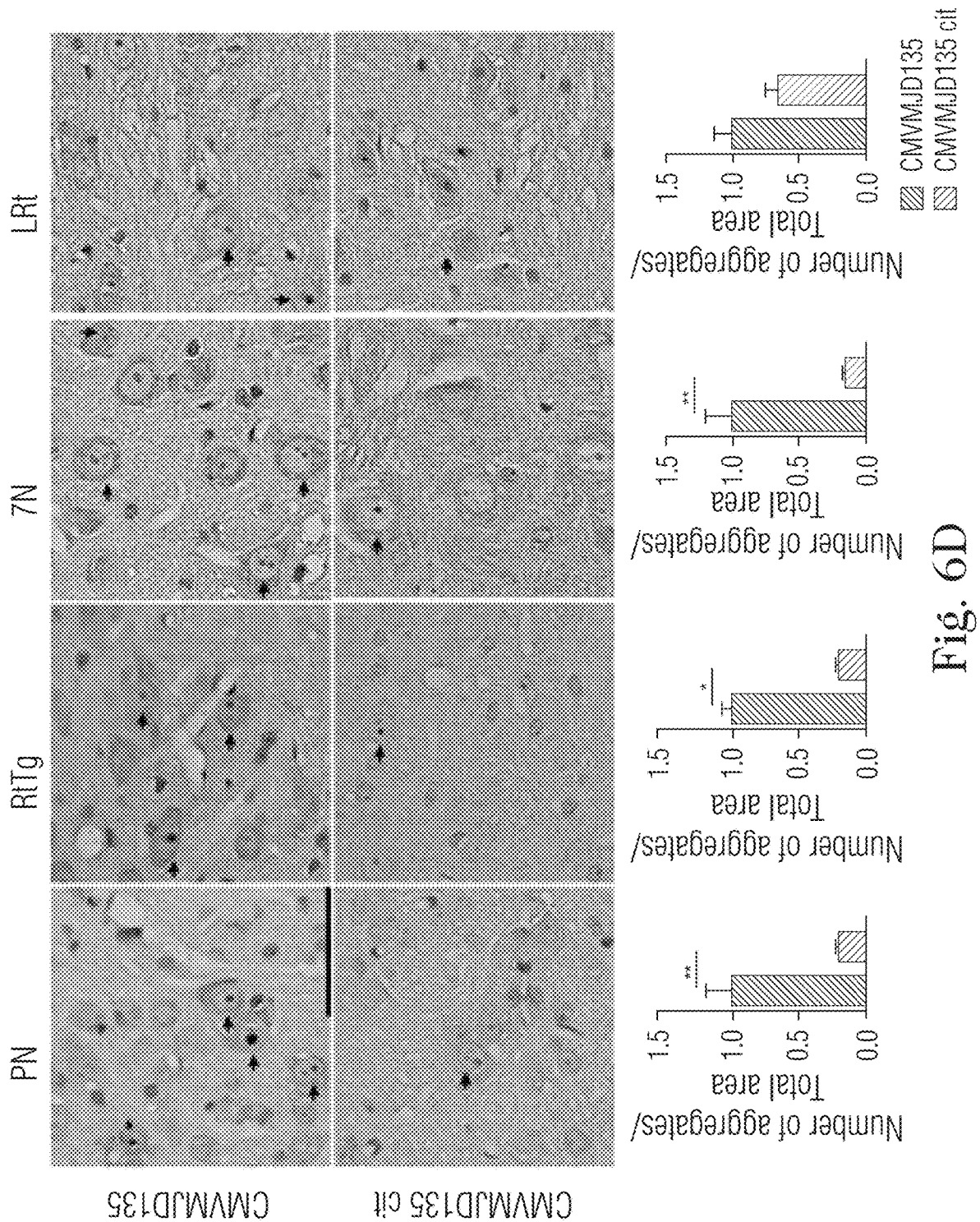
Figure 6E:
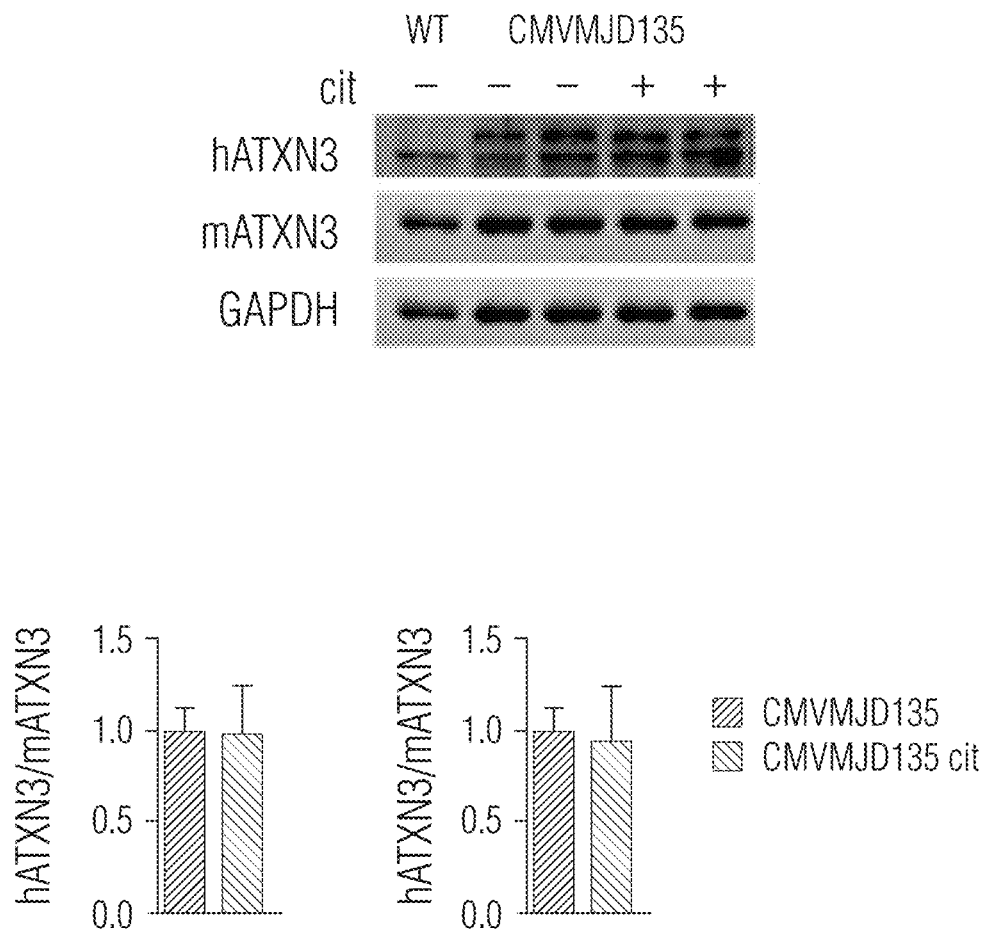

In an embodiment, the analysis of brain tissue from CMVMJD135 mice showed that citalopram treatment (8 mg/kg) mitigated reactive astrogliosis (FIG. 6c) and decreased ATXN3 intranuclear inclusions in the brainstem (FIG. 6d), analogous to the reduction of neuronal aggregates in C. elegans. This reduction was observed in the pontine nuclei (PN), reticulotegmental nuclei of pons (RtTg) and facial motor nuclei (7N) of CMVMJD135 treated mice when compared to their vehicle-treated counterparts (FIG. 6d); the impact of citalopram was less marked in the lateral reticular nuclei (LRt). This reduced ATXN3 aggregation did not correspond to lower levels of ATXN3 protein levels in the brainstem (FIG. 6e), suggesting that the effect of citalopram in mice is similar to that in C. elegans, affecting folding and stability of mutant ATXN3 rather than clearance of the protein.

The present subject-matter show that citalopram and other SSRIs suppressed MJD pathogenesis in the C. elegans and mouse models, showing beneficial effects on motility/coordination, aggregation of mutant ATXN3, and on disease progression. MOD-5 (and SERT) inhibition by citalopram results in increased extracellular 5-HT levels and enhanced serotonergic neurotransmission that can elicit 5-HT dependent effects on neuronal activities, adaptation, and remodeling.

The therapeutic effects of SSRIs for amelioration of mutant ATXN3-mediated neurotoxicity in both C. elegans and mice required chronic treatment; likewise, citalopram prolonged treatment is necessary in depression. Such SSRI treatment modalities result in 5-HT1A autoreceptor desensitization, which inactivates the negative feedback mechanism taking place in pre-synaptic neurons, thereby increasing 5-HT availability and activating postsynaptic receptors. Pindolol, a β-adrenergic receptor partial agonist with 5-HT1A receptor antagonist properties, when combined with SSRIs, results in a significant decrease in time to first response compared with SSRIs alone. Moreover, a faster desensitization of 5-HT1A autoreceptors by a direct agonist (e.g. buspirone) may also accelerate the therapeutic efficacy of SSRIs. Consistently, targeting 5-HT autoreceptors by chronic treatment ameliorated mutant ATXN3-mediated pathogenesis in C. elegans.

The need for chronic and early symptomatic treatment in MJD suggests a neuroprotective mechanism rather than immediate effects on signalling cascades or correction of an imbalance of 5-HT in MJD mice. Moreover, the effect of citalopram and MOD-5 inactivation on aggregation ATXN3 is consistent with an impact of serotonergic neurotransmission on the re-balance of proteostasis state of the organism. Indeed, it has been recently described that the release of serotonin from neurons signals to distal tissues the activation of protective mechanisms to prevent proteotoxicity.

Comparing the effects obtained with citalopram with those described in the literature for other molecules with positive effect in MJD models, this SSRI appears to have a higher therapeutic efficacy. From our own work, when we compare the current results with the previous findings for the Hsp90 inhibitor 17-DMAG (Silva-Fernandes, A. et al. Chronic Treatment with 17-DMAG Improves Balance and Coordination in A New Mouse Model of Machado-Joseph Disease. Neurotherapeutics (2014), we observe a more pronounced therapeutic effect of citalopram. Namely, the manifestation of motor swimming defects was delayed eight weeks by 17-DMAG treatment versus at least 20 weeks by citalopram treatment; also, at 30 weeks, the percentage of effect of 17-DMAG in this test was of 33%, and that of citalopram of 79%. The difference in performance between the treated groups (normalized to the respective non-treated groups) in the two experiments was statistically significant at this age (P=0.018).

In conclusion, the efficacy of citalopram in suppression of ATXN3 pathogenesis in two disease models, as well as its safety record of being widely used in depression patients, prompts us to suggest this drug for clinical trials in MJD patients.

Methods

Nematode strains and general methods. For a list of strains used in this work and name abbreviations, see Table 1. All the strains were backcrossed to Bristol strain N2 five to eight times. Standard methods were used for culturing and observing C. elegans, unless otherwise noted. Nematodes were grown on nematode growth medium (NGM) plates seeded with Escherichia coli OP50 strain at 20° C.

TABLE 1

List of strains, abbreviations and crosses used in this work.

| Strain | Abbreviation | Protein | Genotype |
|---|---|---|---|
| AM510 | AT3q14 | AT3q14::YFP | rmIs228[$P_{F25B3.3}$::AT3v1-1q14::yfp] |
| AM685 | AT3q130 | AT3q130::YFP | rmIs263[$P_{F25B3.3}$::AT3v1-1q130::yfp] |
| AM599 | AT3q130 | AT3q130::YFP | rmIs261[$P_{F25B3.3}$::AT3v1-1q130::yfp] |
| AQ866 | ser-4 | | ser-4(ok512) III |
| MAC72 | ser-4; AT3q130 | AT3q130::YFP | ser-4(ok512) III; rmIs263[$P_{F25B3.3}$::AT3v1- |

TABLE 1-continued

List of strains, abbreviations and crosses used in this work.

| Strain | Abbreviation | Protein | Genotype |
|---|---|---|---|
| MT8944 | mod-5 | | mod-5(n822) I |
| MAC73 | mod-5; AT3q130 | AT3q130::YFP | mod-5(n822) I; rmIs263[P$_{F25B3.3}$ ::AT3v1-1q130::yfp] |
| MT9772 | mod-5 | | mod-5(n3314) I |
| MAC74 | mod-5; AT3q130 | AT3q130::YFP | mod-5(n3314) I; rmIs263[P$_{F25B3.3}$ ::AT3v1-1q130::yfp] |
| DA1814 | ser-1 | | ser-1(ok345) X |
| MAC75 | ser-1; AT3q130 | AT3q130::YFP | ser-1(ok345) X; rmIs263[P$_{F25B3.3}$ ::AT3v1-1q130::yfp] |
| CB1370 | daf-2 | | daf-2(e1370) III |
| CF1038 | daf-16 | | daf-16(mu86) I |

Compounds. All the compounds were obtained from the commercial vendors indicated below and were used without further purification: estrone CAS 53-16-7 (Sigma, USA), fluoxetine CAS 56296-78-7 (Kemprotec Ldt, UK), zimelidine CAS 61129-30-4 (Sigma, USA), lyzergol CAS 602-85-7 (Sigma, USA), pindolol CAS 13523-86-9 (Sigma, USA), trazodone hydrochloride CAS 25332-39-2 (Sigma, USA), citalopram hydrobromide CAS 59729-32-7 (Kemprotec Ldt, UK), escitalopram (S-citalopram) hydrobromide CAS 219861-08-2 (Kemprotec Ldt, UK). Citalopram used for studies in mice and vabicaserin were kindly provided by Lündbeck (Denmark).

Drug Toxicity Assay. Bristol strain N2 was used to assay compound toxicity and determine safe concentrations to use. The assay was performed in 96-well plate format, in liquid culture. Each well contained a final volume of 60 µL, comprising 20-25 animals in egg stage, drug at the appropriate concentration and OP50 bacteria to a final OD$_{595nm}$ of 0.6-0.8 measured in the microplate reader (Bio-Rad microplate reader 680). To obtain the age synchronized population of eggs, gravid adults were treated with alkaline hypochlorite solution (0.5 M NaOH, ~2.6% NaClO) for 7 min. The animals were then washed in M9 buffer, resuspended in S-medium to the appropriate egg number and transferred into the 96 well-plate. The OP50 bacteria were grown overnight at 37° C. and 150 rpm in Luria Broth (LB) media, pelleted by centrifugation, inactivated by 4-6 cycles of freeze/thaw, frozen at −80° C. and then resuspended in S-medium supplemented with cholesterol, streptomycin, penicillin and nystatin (Sigma, USA). Worms were grown with continuous shaking at 180 rpm at 20° C. (Shel Lab) during 7 days. Compounds were prepared in 100% DMSO (Sigma, USA) and tested at dilutions corresponding to a maximum concentration of 1% DMSO to avoid solvent-specific developmental defects and toxicity. For each compound, two final concentrations were tested (50 µM and 25 µM). The effect of compounds on C. elegans physiology was monitored by the rate at which the E. coli food suspension was consumed, as a read out for C. elegans growth, survival or fecundity. The absorbance (OD$_{595nm}$) was measured daily. OP50-only (S-medium, no vehicle) and DMSO 1% (vehicle) controls were used.

C. elegans assays for motility defects and aggregation. Animals (N2, AT3 WT or AT3q130) were grown in liquid culture in a 96-well plate format, with the chemical compounds, as described above. Four day old animals were transferred from the 96-well plates onto an unseeded NGM plate (equilibrated at 20° C.). Plates were allowed to dry for 1 hour before starting the assays. Motility assays were performed at 20° C. as previously described. Motor behaviour assays were run in triplicates or quadruplicates (n=3 or 4), with a total of at least 150 animals tested per genotype and/or compound. For confocal dynamic imaging and quantification of ATXN3 aggregation, live animals were immobilized with 3 mM levamisole (Sigma, USA) and mounted on a 3% agarose pad. All images were captured on an Olympus FV1000 (Japan) or Zeiss LSM 510 (Germany) confocal microscopes, under a 60× oil (NA=1.35) or 63× water (NA=1.0) objectives. Z-series imaging was acquired for all vehicle- and compound-treated animals, using a 515/514 nm laser excitation line for YFP fusion proteins. The pinhole was adjusted to 1.0 Airy unit of optical slice, and a scan was acquired every~0.5 µm along the Z-axis. For quantification of aggregates three parameters were measured: area of aggregates/total area; number of aggregates/total area and number of aggregates. Values shown are the mean (normalized to vehicle treated control) of eight or more animals per group, unless noted otherwise.

C. elegans citalopram time course assays. For time course experiments, animals were grown on NGM plates with OP50 supplemented with citalopram. OP50 cultures were prepared as described above and concentrated 10× with S-media supplemented with streptomycin, penicillin and nystatin (Sigma). Stock solutions of citalopram (2.5 mM and 0.5 mM) (Kemprotec, UK) or vehicle (DMSO, Sigma, USA) were prepared and added to OP50 cultures to a final concentration of 25 µM or 5 µM. Plates were seeded with 200 µL of OP50-citalopram/vehicle and left at room temperature (RT) to dry for at least three days. Fresh plates were prepared two to three times a week to prevent drug degradation. Off-drug effect was evaluated by treating the animals for four days and after that time animals were transferred to DMSO plates (vehicle). During the reproductive period, animals were transferred into new fresh plates every day.

Immunobloting analysis. For determination of the steady-state protein levels of ATXN3, the animals were incubated in liquid culture with citalopram in a 96-well plate format as described above. Four day old animals were transferred from the liquid culture onto an unseeded NGM plate (equilibrated at 20° C.). After 1 hour of acclimation 25 individual young adult animals were picked, boiled for 15 min in SDS sample buffer (in order to destroy all the aggregates) and the resulting extracts resolved on a 10% SDS gel, as previously described. Immunoblots were probed with anti-ATXN3 mouse (1H9, MAB5360, Milipore, USA; 1:1000 or 1:150) and anti-tubulin mouse antibodies (T5168, Sigma, USA; 1:5000); and detected with horseradish peroxidase-coupled secondary antibodies (Biorad, USA) and chemiluminescence (ECL Western-blotting detecting reagents, Amersham Pharmacia, UK). Protein isolation from mouse brainstem tissue and Western-blot were performed as previously described by our group. The blots were blocked and incubated overnight at 4° C. with the primary antibody rabbit anti-ataxin-3 serum (kindly provided by Dr. Henry Paulson) (1:5000) and mouse anti-GAPDH (G8795, Sigma, USA, 1:1000). As a loading control, mouse ataxin-3 and GAPDH were used. Western-blot quantifications were performed using Chemidoc XRS Software with ImageLab Software (Biorad, USA) or Image J software (NIH, USA), according to the manufacturer's instructions. ATXN3 fractionation assays were performed as previously described, with the following modifications: AT3q130 animals were grown for four days in NGM-citalopram/vehicle plates. Nematodes were collected and washed in M9 buffer, and ressuspended in RIPA buffer (50 mM Tris, 150 mM NaCl, 0.2% Triton X-100, 25 mM EDTA, supplemented with complete protease inhibitor (Roche, USA)) before shock freezing in liquid nitrogen. After three freeze-thawing cycles, the worm pellet was ground with a motorized pestle, and lysed on ice, in the presence of 0.025 U/mL benzonase (Sigma, USA). The lysate was centrifuged at 1000 rpm for 1 min in a tabletop centrifuge to pellet the carcasses. Protein concentration was determined using Bradford assay (Bio-Rad, USA) and was set to a final concentration of 3-4 µg/µL in all experimental conditions and followed by a 22,000 g centrifugation for 30 min at 4° C. The pellet fractions were separated from supernatants (Triton X-100-soluble fraction) and homogenized in 150 µl RIPA buffer containing 2% SDS followed by a second centrifugation step at RT. The supernatants (SDS-soluble fraction) were removed, and the remaining pellets were incubated for 16 h in 100% formic acid (FA) at 37° C. After FA evaporation at 37° C., the pellet was dissolved in 25 µL Laemmli-buffer (SDS-insoluble fraction) followed by pH adjustment with 2 M Tris-base for SDS-PAGE analysis. Gels were loaded with 50 µg of the Triton X-100 fraction, 40 µL of the SDS-soluble fraction and the complete SDS-insoluble fraction. Western-blot analyses were performed as described above.

Lifespan. Assays were performed at 20° C. as previously described. Approximately 100 hermaphrodites were cultured on each Petri dish and were transferred to fresh plates every day until the cessation of progeny production, and about every 1-3 days thereafter. Animals were scored as dead if they showed no spontaneous movement or response when prodded. Dead animals that displayed internally hatched progeny, extruded gonad or desiccation were excluded.

Transgenic mouse model and drug administration. CMVMJD135 mice were generated as described previously. DNA extraction, animal genotyping and CAG repeat size analyses were performed as previously described. The mean repeat size (±s.d.) for all mice used was 130±2. Age-matched and genetic background-matched WT animals were used as controls. Only male mice were used in this study. We administrated citalopram hydrobromide CAS 59729-32-7 (Lundbeck, Denmark) in the drinking water at two doses (8 and 13 mg/kg/day) that roughly equate to the high dosage range prescribed to human patients for depression. Treatment was initiated at five weeks of age, one week before the expected onset of the first neurological symptoms. The trial was ended at 34 weeks of age, according to the humane endpoints established for the non-treated CMVMJD135 mice. All animal procedures were conducted in accordance with European regulations (European Union Directive 86/609/EEC). Animal facilities and the people directly involved in animal experiments (ATC, SE, ASF, SDS) were certified by the Portuguese regulatory entity-Direcção Geral de Alimentação e Veterinária. All of the protocols performed were approved by the Animal Ethics Committee of the Life and Health Sciences Research Institute, University of Minho.

Neurochemical quantification. CMVMJD135 and WT male littermate mice (n=5-8) were sacrificed at 24 weeks of age by decapitation, their brains were rapidly removed, snap frozen in liquid nitrogen and dissected. 5-HT and 5-hydroxyindoleacetic acid (5-HIAA) levels were measured in the substantia nigra, medulla oblongata and cerebellum by high performance liquid chromatography, combined with electrochemical detection (HPLC/EC), as described previously. Concentrations of neurotransmitters were calculated using standard curves and results were expressed in terms of 5-HT and metabolite content per amount of protein.

Behavioural assessment. Behavioural analysis was performed during the diurnal period in groups of five males per cage, including CMVMJD135 hemizygous transgenic mice and WT littermates (n=13-16 per genotype) treated with citalopram or with vehicle (water). All behavioural tests started in a pre-symptomatic stage (4 weeks) and were conducted until 30 or 34 weeks of age (FIG. 5a). Neurological tests and general health assessment were performed using the SHIRPA protocol, enriched with the hanging wire test. The dragging of the paws and the stride length were evaluated with footprinting analysis. Motor behaviour was further assessed using the balance beam walk test (12 mm square and 17 mm round beams) and the motor swimming test. All behavioural tests were performed as previously described (Silva-Fernandes, A. et al. Chronic Treatment with 17-DMAG Improves Balance and Coordination in A New Mouse Model of Machado-Joseph Disease. Neurotherapeutics (2014). Body weight was also registered for each evaluation time point.

Immunohistochemistry and quantification of neuronal inclusions. Thirty four week-old WT and CMVMJD135 littermate mice, vehicle- and citalopram-treated (n=4 for each group) were deeply anesthetized- with a mixture of ketamine hydrochloride (150 mg/kg) plus medetomidine (0.3 mg/kg) and transcardially perfused with phosphate-buffered saline (PBS) followed by 4% paraformaldehyde (PFA) (Panreac, USA). Brains were removed and post fixed overnight in PFA and embedded in paraffin. Slides with 4 µm-thick paraffin sections were subjected to antigen retrieval and then incubated with mouse anti-ATXN3 (1H9, MAB5360, Milipore, USA; 1:100) or rabbit anti-GFAP (DAKO Corporation, Carpinteria; 1:1000) which were detected by incubation with a biotinylated anti-polyvalent antibody, followed by detection through biotin-streptavidin coupled to horseradish peroxidase and reaction with the DAB (3,3'-diaminobenzidine) substrate (Lab Vision™ Ultra-Vision™ Detection kit, Thermo Scientific). The slides were counterstained with hematoxylin 25% according to standard procedures. ATXN3 positive inclusions in the pontine nuclei (PN), reticulotegmental nucleus of the pons (RtTg), facial motor nucleus (7N) and lateral reticular nucleus (LRt); and stained astrocytes (GFAP-positive) in the substantia nigra (SN) of either vehicle or citalopram treated animals (n=4 for each conditions, 4 slides per animal) were quantified and normalized for total area using the Olympus BX51 stereological microscope (Olympus, Japan) and the Visiopharma integrator system software (Visopharm, Denmark) as previously described.

Statistical analysis. Data was analyzed through the non-parametric Mann-Whitney U-test when variables were non-continuous or when a continuous variable did not present a normal distribution (Kolmogorov-Smirnov test, P<0.05). Continuous variables with normal distributions and with homogeneity of variance (Levene's test) were analyzed with Repeated-Measures ANOVA for longitudinal multiple comparisons and One-Way ANOVA or Student's t-test for paired comparisons, using Tukey or Bonferroni tests for post-hoc comparisons. When these two latter assumptions were not assumed, an appropriate data transformation (e.g., logarithmic) was applied, and the data were reanalyzed (body weight, balance beam walk test and motor swimming test). When logarithmic data transformation did not reduce the heterogeneity of variances (hanging wire test), several mathematical models were applied. In this test, the best fit model was the logarithmic and the treatment differences were analyzed according the R squares of the CMVMJD135 groups, with a normal residual distribution. Statistical analysis of *C. elegans* survival assays was performed using the log rank (Mantel-Cox) test. All statistical analyses were performed using SPSS 20.0/22.0 (SPSS Inc., Chicago, Ill.) and G-Power 3.1.9.2 (University Kiel, Germany). A critical value for significance of $P<0.05$ was used throughout the study.

The present invention is not, obviously, in any way restricted to the herein described embodiments and a person with average knowledge in the area can predict many possibilities of modification of the same invention and substitutions of technical characteristics by others equivalent, depending on the requirements of each situation, as defined in the appended claims.

The embodiments described above can be combined with each other. The following claims further define the preferred embodiments of the present invention.

The invention claimed is:

1. A method of treating Machado-Joseph disease, comprising administering a therapeutically effective amount of citalopram, escitalopram or pharmaceutically acceptable salts thereof, wherein the therapeutically effective amount is a dosage of 20-40 mg/day.

2. The method of claim 1, wherein the treatment of a Machado-Joseph disease is to improve the motor symptoms of balance, motor coordination, and/or motor performance.

3. The method of claim 1, wherein the citalopram, escitalopram, or pharmaceutically acceptable salts thereof is administered orally.

4. The method of claim 1, wherein the therapeutically effective amount is a dosage of less than 40 mg/day.

5. The method of claim 1, wherein the therapeutically effective amount is a dosage 30-38 mg/day.

6. The method of claim 1, wherein the step of administering the citalopram, escitalopram, or pharmaceutically acceptable salts thereof is via a tablet or a suppository.

7. The method of claim 1, wherein the step of administering the citalopram, escitalopram, or pharmaceutically acceptable salts thereof is performed with a single dose.

8. A method of treating Machado-Joseph disease, the method consisting of administering a therapeutically effective amount of citalopram, escitalopram, or pharmaceutically acceptable salts thereof and a pharmaceutical acceptable carrier, adjuvant, excipient or mixture thereof.

* * * * *